US009977861B2

(12) United States Patent
Rigatti et al.

(10) Patent No.: US 9,977,861 B2
(45) Date of Patent: May 22, 2018

(54) METHODS AND SYSTEMS FOR DETERMINING HAPLOTYPES AND PHASING OF HAPLOTYPES

(71) Applicant: ILLUMINA CAMBRIDGE LIMITED, Essex (GB)

(72) Inventors: Roberto Rigatti, Essex (GB); Jonathan Mark Boutell, Essex (GB)

(73) Assignee: Illumina Cambridge Limited (GB)

( * ) Notice: Subject to any disclaimer, the term of this patent is extended or adjusted under 35 U.S.C. 154(b) by 815 days.

(21) Appl. No.: 13/793,676

(22) Filed: Mar. 11, 2013

(65) Prior Publication Data

US 2014/0024537 A1 Jan. 23, 2014

Related U.S. Application Data

(60) Provisional application No. 61/673,052, filed on Jul. 18, 2012.

(51) Int. Cl.
*C12Q 1/68* (2018.01)
*G06F 19/22* (2011.01)

(52) U.S. Cl.
CPC .......... *G06F 19/22* (2013.01); *C12Q 1/6869* (2013.01); *C12Q 2525/117* (2013.01)

(58) Field of Classification Search
CPC .......... C07H 21/00; C12P 19/34; C12Q 1/68; C12Q 1/6869
See application file for complete search history.

(56) References Cited

U.S. PATENT DOCUMENTS

| | | | | |
|---|---|---|---|---|
| 7,569,348 B2 * | 8/2009 | Magness | G06F 19/22 435/6.11 |
| 2004/0005294 A1 * | 1/2004 | Lee | G01N 33/57423 424/93.2 |
| 2004/0072199 A1 | 4/2004 | Brem | |
| 2004/0175702 A1 | 9/2004 | Magness et al. | |
| 2004/0259229 A1 | 12/2004 | Thevelein et al. | |
| 2005/0202490 A1 * | 9/2005 | Makarov | C12N 15/1072 435/6.12 |
| 2007/0122805 A1 * | 5/2007 | Cantor | C12Q 1/6827 435/6.11 |
| 2010/0184075 A1 * | 7/2010 | Cantor | C12Q 1/6827 435/6.18 |
| 2011/0124518 A1 * | 5/2011 | Cantor | C12Q 1/6816 506/9 |

FOREIGN PATENT DOCUMENTS

| | | | |
|---|---|---|---|
| JP | 2009215171 | A | 9/2009 |
| JP | 2010538618 | A | 12/2010 |
| WO | 2004/042078 | | 5/2004 |
| WO | 2011/106368 | | 9/2011 |
| WO | 2011/157846 | | 12/2011 |
| WO | 2014013218 | A1 | 1/2014 |

OTHER PUBLICATIONS

Xi et al. (BMC bioinformatics 10.1 (2009): 232; 9 pages).*
Dizdaroglu et al.( Nucleic acids research 29.3 (2001): e12; 8 pages).*
Browning, et al., "Haplotype phasing: existing methods and new developments", Nature Reviews, Genetics. vol. 12, Oct. 2011, pp. 703-714.
Zhang,et al., "Long-range polony haplotyping of individual human chromosome molecules", Nature Genetics. vol. 38, No. 3, pp. 382-387.
Cheng et al., "8-Hydroxyguanine, an Abundant Form of Oxidative DNA Damage, Causes G -> T and A -> C Substitutions", The Journal of Biological Chemistry, vol. 267, No. 1, Jan. 5, 1992, 166-172.
Clark et al., "High sensitivity mapping of methylated cytosines", Nucleic Acids Research, vol. 22, No. 15, 1994, 2990-2997.
Dapprich et al., "SNP-specific extraction of haplotype-resolved targeted genomic regions", Nucleic Acids Research, vol. 36, No. 15, 2008, e94, 9 pages.
Haines et al., "Allele-Specific Non-CpG Methylation of the Nf1 Gene during Early Mouse Development", Developmental Biology 240, 2001, 585-598.
Johnson et al., "A third base pair for the polymerase chain reaction: inserting isoC and isoG", Nucleic Acids Research, vol. 32, No. 6, 2004, 1937-1941.
Le Page et al., "Repair and mutagenic potency of 8-oxoG:A and 8-oxoG:C base pairs in mammalian cells", Nucleic Acids Research, vol. 26, No. 5, 1998, 1276-1281.
Lee et al., "Non-Natural Nucleotides as Probes for the Mechanism and Fidelity of DNA Polymerases", Biochim Biophys Acta., 1804(5), May 2010, 1064-1080.
Lister et al., "Human DNA methylomes at base resolution show widespread epigenomic differences", Nature, 462(7271), Nov. 19, 2009, 315-322.
Petrie et al., "Deep sequencing analysis of mutations resulting from the incorporation of dNTP analogs", Nucleic Acids Research, vol. 38, No. 22, 2010, 8095-8104.
Pritchard et al., "A general model of error-prone PCR", Journal of Theoretical Biology 234, 2005, 497-509.
Ramsahoye et al., "Non-CpG methylation is prevalent in embryonic stem cells and may be mediated by DNA methyltransferase 3a", PNAS, vol. 97, No. 10, May 9, 2000, 5237-5242.
Sismour et al., "The use of thymidine analogs to improve the replication of an extra DNA base pair: a synthetic biological system", Nucleic Acids Research, vol. 33, No. 17, 2005, 5640-5646.

(Continued)

*Primary Examiner* — Ethan C Whisenant
(74) *Attorney, Agent, or Firm* — Fletcher Yoder, P.C.

(57) ABSTRACT

The present disclosure provides methods and systems for determining and/or characterizing one or more haplotypes and/or phasing of haplotypes in a nucleic acid sample. In particular, the disclosure provides methods for determining a haplotype and/or phasing of haplotypes in a nucleic acid sample by incorporating synthetic polymorphisms into fragments of a nucleic acid sample and utilizing the synthetic polymorphisms in determining one or more haplotypes and/or phasing of haplotypes.

20 Claims, 19 Drawing Sheets

(56) References Cited

OTHER PUBLICATIONS

Brownlie, et al., "The Caenorhabditis briggsae genome contains active CbmaT1 and Tcb1 transposons," Molecular Genetics and Genomics, vol. 273, 2005, 92-101.
Keith, et al., "Algorithms for Sequence Analysis via Mutagenesis," Bioinformatics, vol. 20 No. 15; published online doi:10.1093/bioinformatics/bth258, May 14, 2004, 2401-2410.
Keith, et al., "Unlocking Hidden Genomic Sequence," Nucleic Acids Research, vol. 32, No. 3, published online DOI: 10.1093/nar/gnh022, Feb. 18, 2004, e35.
Ooka, et al., "Inference of the impact of insertion sequence (IS) elements on bacterial genome diversification through analysis of small-size structural polymorphisms in *Escherichia coli* O157 genomes," Genome Research, vol. 19, 2009, 1809-1816.
Sipos, et al., "An Improved Protocol for Sequencing of Repetitive Genomic Regions and Structural Variations Using Mutagenesis and Next Generation Sequencing," PLoS One 7(8), published online doi:10.1371/journal.pone.0043359, Aug. 17, 2012, e43359.
Clontech, "Diversify® PCR Random Mutagenesis Kit User Manual," Cat. No. 630703, Jan. 23, 2008.
JP Office Action dated May 17, 2016 in counterpart Japanese Application No. JP-2015-522158.
Kitzman et al. "Haplotype-resolved genome sequencing of a Gujarati Indian individual", Nature Biotechnology, 2011, vol. 29, No. 1, p. 59-63.
Peters et al., "Accurate whole-genome sequencing and haplotyping from 10 to 20 human cells", Nature, Jul. 12, 2012, vol. 487, p. 190-195.
Zhen-Chuan Fan et al., "An improved reverse genetics system for generation of bovine viral diarrhea virus as a BAC cDNA", Journal of Virological Methods, 2008, vol. 149, p. 309-315; doi:10.1016/j.viromet.2008.01.011.

* cited by examiner

Naturally occurring SNP

Allele 1 acgttGcttaagcttactttactataattttggccttacgaaccgggttaccgatacccgagactagctagctaccccgcagctacgactcg
atctcagcatcgatcgtcgatcgcgcgtacaaacacgcatcgcatacgactcgtacttttttttttacgatcgatcatcgactcgatcttttacg
ctcgtacgccatctatctatctatctcttcatcttctctccccccatcactcctacgactgcgatcgacgcgtacgcatcgcgcgcgggggg
gctacgatcgagctagctcagctacggttagctacgggcatctagctgcctgacgatcgatctactagcggacttgctgtgcggcgctact
attacgcagcgactagatcgggcgcgtcgtcgatcgacgcagcgcgggggactatcgatcattttttttactgacgatcgatcgcgcggc
tatcctcgagcgtcgacgtactgtctcgcgtatacgcgtcacgtagcgagctactcgcgcgctatgctagctgtttttctctgatctacgccc
aaaaatcctatcgatcgtcgatctagcgctacgtactcgcgcggggcgctatcgagctactgcgatcgatcgctttcttcgatctcggactt
acgatcgacgcttttcgatcatcgatgctacgatcaaaaactatatgcgtacgattcgctagctacttttctatctagcgacgtacgactctga
cgtactgactacttacgcgctacgctcgatcgatcgatcctcgctatcgatcgattcgctagcattcgctacgtgctagctagctagcctcta
tcgatccgtagctagcagctcgtgacgtacgactatcgatccggcgggcgcgctatcgagagaaaatctcgcgcgggggggcgattcc
ggaatcgaatcgcgatatcgcgagcattccatatatctatatctgagagctactatgcagctgatctagcgctacgatcgatgctgcttatca
tcatgacacgtcagcatagcgatcgactacgtacgtcgatcgtacgatcgcggcatacactcagcgatagctgctagctactgatccatttt
tttatcagtcatctgcgatcgatcgacgcatagccatgcactctcagatcgcgcgatgcgacgtacgttacgagcatcgcttaaaaatctat
atcgctgccccgcggggcgatcgcatatgccgtacgatcctgtcgtactcgtagtacgctagcgctatcgctagctgatcgctacgcagt
ctgacgcgcatagcgactcatcagcgctacgttgcgctacgtcgcgtactcagtC

Naturally occurring SNP

Naturally occurring SNP

Artificial SNPs

Allele 1 acgttGcttaagcTtactttactataattttggccttacgaaccgggttaccgatacccgagacTagctagctaccccgcagcta
cgactcgatcTcagcatcgatcgtcgatcgcgcgtacaaacacgcatcgcatacgactcgtacttttttttttacgatcgatcatcga
cTcgatcttttacgctcgtacgccatctatctatctatctcttcatcttctcTccccccatcactcctacgactgcgatcgacgcgtac
gcatcgcgcgcgggggggctacgatcgagctagctcagctacggttagctacgggcatctagctgcctgacgatcgatctacta
gcggacttgcTgtgcggcgctactattacgcagcgacTagatcgggcgcgtcgtcgatcgacgcagcgcgggggacTatc
gatcattttttttactgacgatcgatcgcgcggctatccTcgagcgtcgacgtactgtctcgcgtatacgcgtcacgtagcgagcta
ctcgcgcgcTatgctagctgtttttctctgatctacgcccaaaaatcctatcgatcgtcgatctagcgctacgtactcgcgcggggc
gctatcgagctactgcgatcgatcgctttcTtcgatcTcggacttacgatcgacgcttttcgatcatcgatgcTacgatcaaaaac
tatatgcgtacgattcgctagctacttttctatctagcgacgtacgactctgacgtactgactacTtacgcgctacgctcgatcgatc
gatcctcgctatcgatcgattcgcTagcattcgctacgtgctagctagctagcctctatcgatccgtagctagcagctcgtgacgta
cgactatcgatccggcgggcgcgctatcgagagaaaatcTcgcgcgggggggcgattccggaatcgaatcgcgatatcgcga
gcattccatatatctatatctgagagctactatgcagctgatctagcgctacgatcgatgcTgcttatcatcatgacacgtcagcata
gcgatcgacTacgtacgtcgatcgtacgatcgcggcatacactcagcgatagctgctagctactgatccatttttttatcagtcatct
gcgatcgatcgacgcatagccatgcactctcagatcgcgcgatgcgacgtacgttacgagcatcgcTtaaaaatctatatcgctg
ccccgcggggcgatcgcatatgccgtacgatcctgtcgtactcgtagtacgctagcgcTatcgctagctgatcgctacgcagtct
gacgcgcatagcgacTcatcagcgctacgttgcgctacgtcgcgtactcagtC

Artificial SNP

Naturally occurring SNP

Naturally occurring SNP

Allele 2 acgttTcttaagcttactttactataattttggccttacgaaccgggttaccgatacccgagactagctagctaccccgcagctacgactc
gatctcagcatcgatcgtcgatcgcgcgtacaaacacgcatcgcatacgactcgtacttttttttttacgatcgatcatcgactcgatctttta
cgctcgtacgccatctatctatctatctcttcatcttctctcccccccatcactcctacgactgcgatcgacgcgtacgcatcgcgcgcgggg
gggctacgatcgagctagctcagctacggttagctacgggcatctagctgcctgacgatcgatctactagcggacttgctgtgcggcgc
tactattacgcagcgactagatcgggcgcgtcgtcgatcgacgcagcgcgggggactatcgatcatttttttactgacgatcgatcgcg
cggctatcctcgagcgtcgacgtactgtctcgcgtatacgcgtcacgtagcgagctactcgcgcgctatgctagctgtttttctctgatcta
cgcccaaaaatcctatcgatcgtcgatctagcgctacgtactcgcgcggggcgctatcgagctactgcgatcgatcgctttcttcgatctc
ggacttacgatcgacgcttttcgatcatcgatgctacgatcaaaaactatatgcgtacgattcgctagctacttttctatctagcgacgtacg
actctgacgtactgactacttacgcgctacgctcgatcgatcgatcctcgctatcgatcgattcgctagcattcgctacgtgctagctagct
agcctctatcgatccgtagctagcagctcgtgacgtacgactatcgatccggcgggcgcgctatcgagagaaaatctcgcgcggggg
ggcgattccggaatcgaatcgcgatatcgcgagcattccatatatctatatctgagagctactatgcagctgatctagcgctacgatcgat
gctgcttatcatcatgacacgtcagcatagcgatcgactacgtacgtcgatcgtacgatcgcggcatacactcagcgatagctgctagct
actgatccattttttatcagtcatctgcgatcgatcgacgcatagccatgcactctcagatcgcgcgatgcgacgtacgttacgagcatcg
cttaaaaatctatatcgctgccccgcggggcgatcgcatatgccgtacgatcctgtcgtactcgtagtacgctagcgctatcgctagctga
tcgctacgcagtctgacgcgcatagcgactcatcagcgctacgttgcgctacgtcgcgtactcagtA

Naturally occurring SNP

Naturally occurring SNP

Artificial SNPs

Allele 2 acgttTcttaagcTtactttactataattttggccttacgaaccgggttaccgatacccgagactagctagcTaccccgcagcta
cgactcgatctcagcatcgatcgtcgatcgcgcgtacaaacacgcatcgcatacgacTcgtactttttttttacgatcgatcatcg
acTcgatcttttacgctcgtacgccatctatctatctatctcttcatcttctcTcccccatcactcctacgactgcgatcgacgcgt
acgcatcgcgcgcgggggggggctacgatcgagctagctcagctacggttagcTacgggcatctagctgcctgacgatcgatct
actagcggacttgcTgtgcggcgctactattacgcagcgactagatcgggcgcgtcgtcgatcgacgcagcgcgggggacT
atcgatcatttttttactgacgatcgatcgcgcggctatcctcgagcgtcgacgtactgtctcgcgtatacgcgtcacgtagcgagc
tactcgcgcgctatgctagctgtttttctcTgatctacgcccaaaaatcctatcgatcgtcgatcTagcgctacgtactcgcgcgg
ggcgctatcgagctactgcgatcgatcgctttcttcgatctcggacttacgatcgacgcttttcgatcatcgatgctacgatcaaaaa
ctatatgcgtacgattcgctagctacttttctatcTagcgacgtacgactctgacgtactgactacttacgcgctacgctcgatcgat
cgatccTcgctatcgatcgattcgctagcattcgctacgtgctagctagctagcctctatcgatccgtagctagcagctcgtgacg
tacgacTatcgatccggcgggcgcgctatcgagagaaaatcTcgcgcggggggggcgattccggaatcgaatcgcgatatcg
cgagcattccatatatctatatctgagagctactatgcagctgatctagcgctacgatcgatgcTgcttatcatcatgacacgtcag
catagcgatcgacTacgtacgtcgatcgtacgatcgcggcatacactcagcgatagctgctagcTactgatccatttttttatca
gtcatcTgcgatcgatcgacgcatagccatgcactctcagatcgcgcgatgcgacgtacgttacgagcatcgcTtaaaaatct
atatcgctgccccgcggggcgatcgcatatgccgtacgatcctgtcgtacTcgtagtacgctagcgctatcgctagctgatcgc
TacgcagtctgacgcgcatagcgactcatcagcgcTcgttgcgctacgtcgcgtactcagtA

Artificial SNP

Naturally occurring SNP

FIG. 7
A) Lane 1
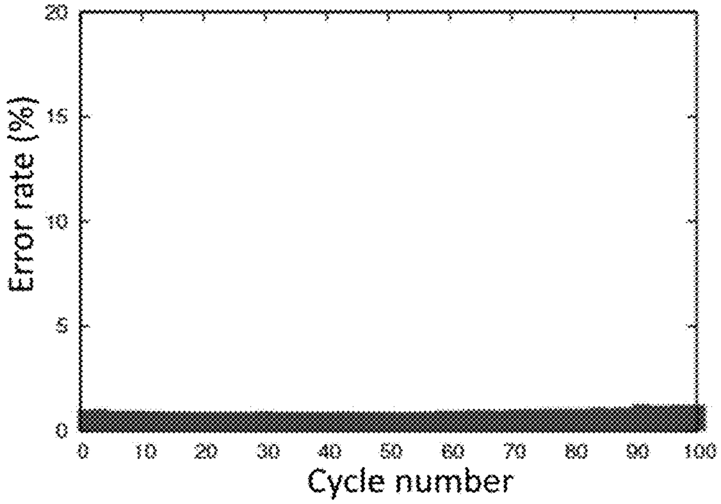
B) Lane 2
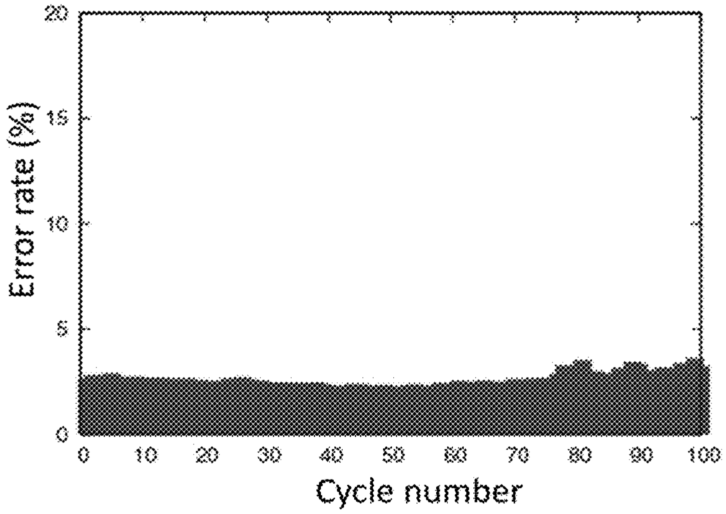

FIG. 7 (cont.)
C) Lane 3
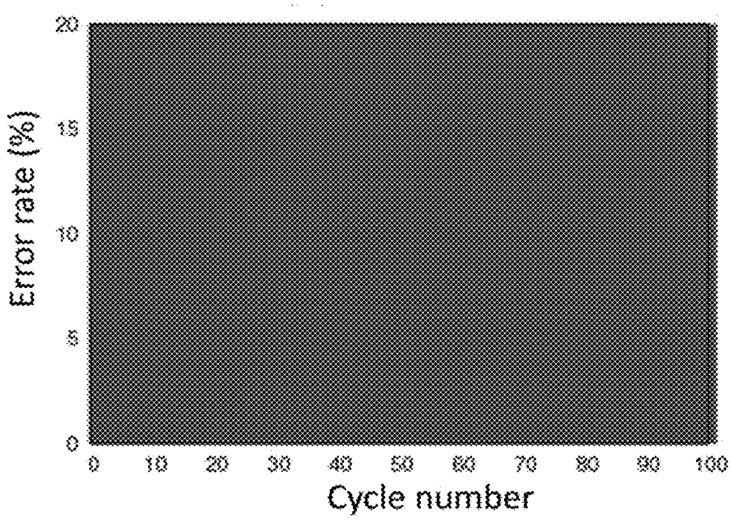
D) Lane 4
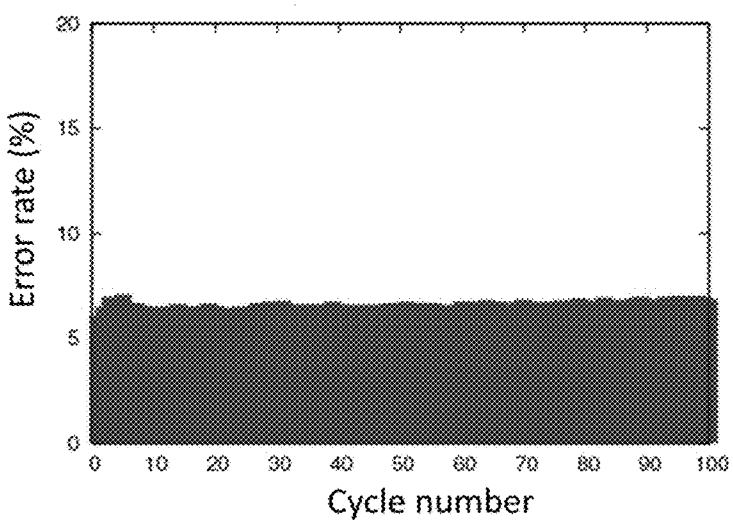

FIG. 8
A) Lane 1
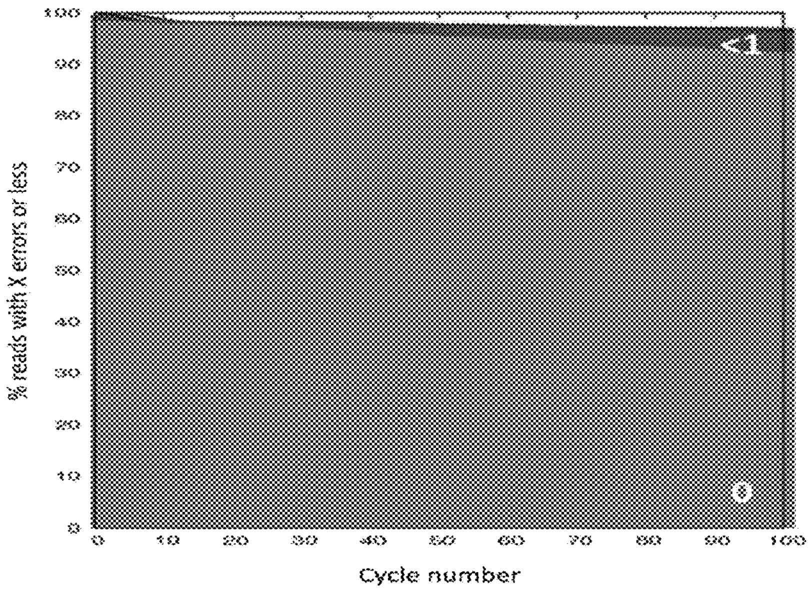
B) Lane 2
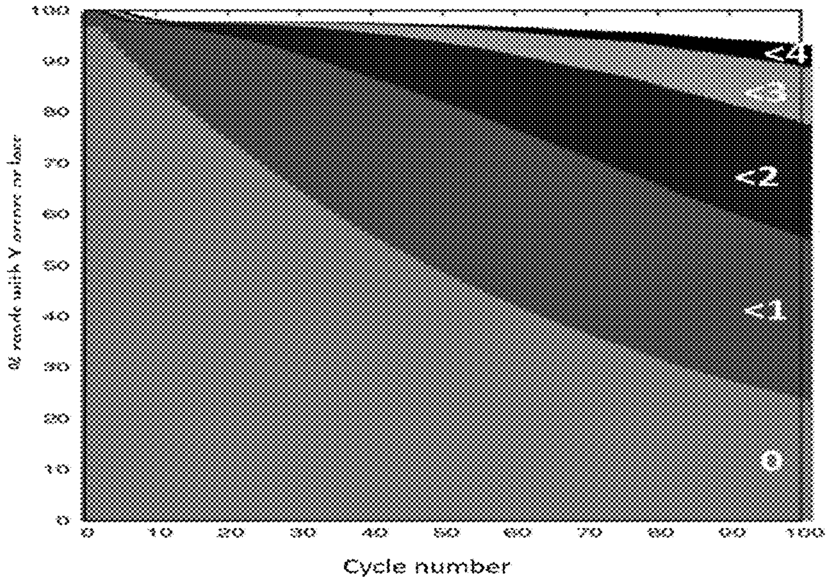

FIG. 8 (cont.)
C) Lane 3
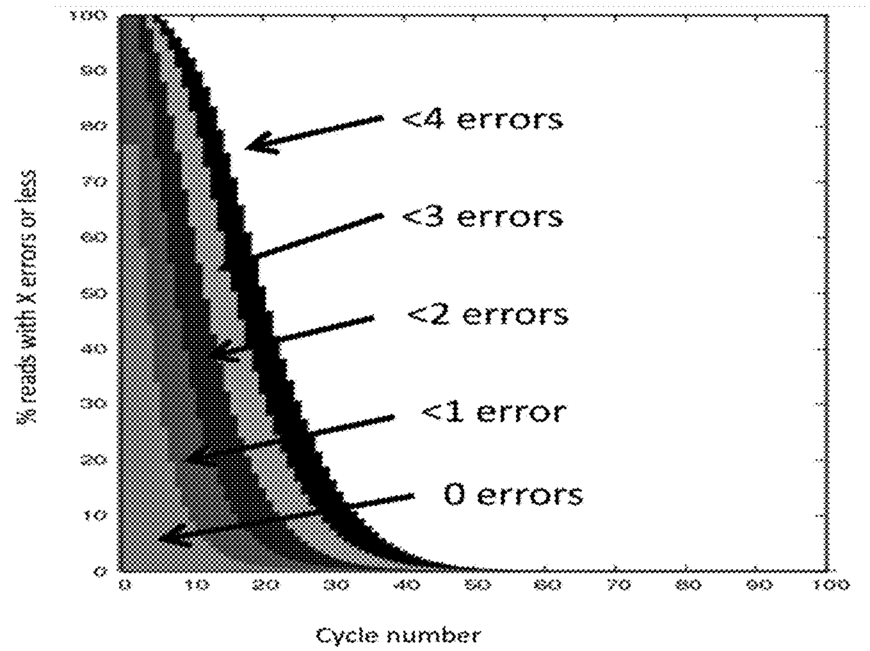
D) Lane 4
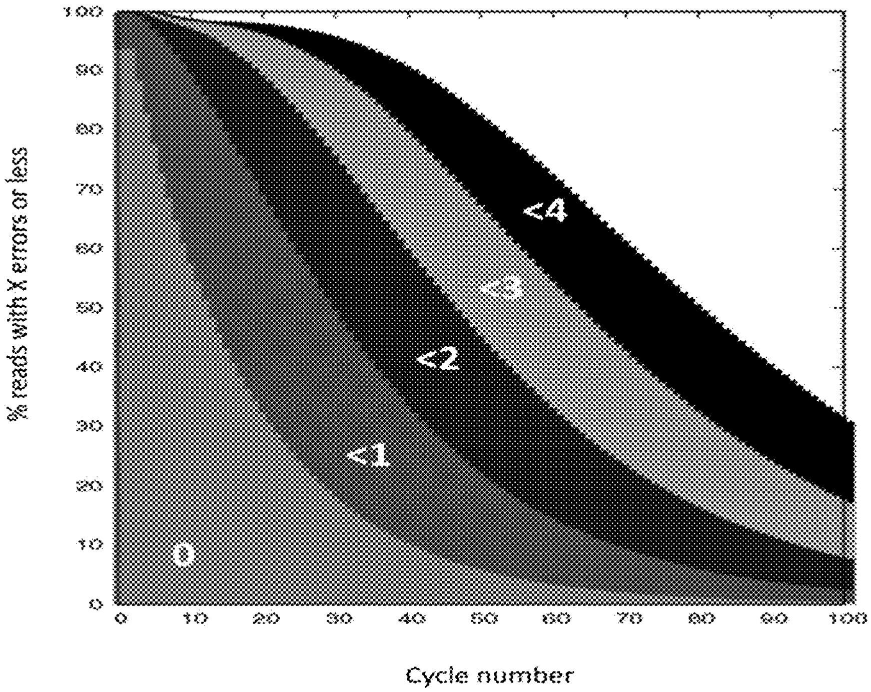

FIG. 10
A) Lane 2
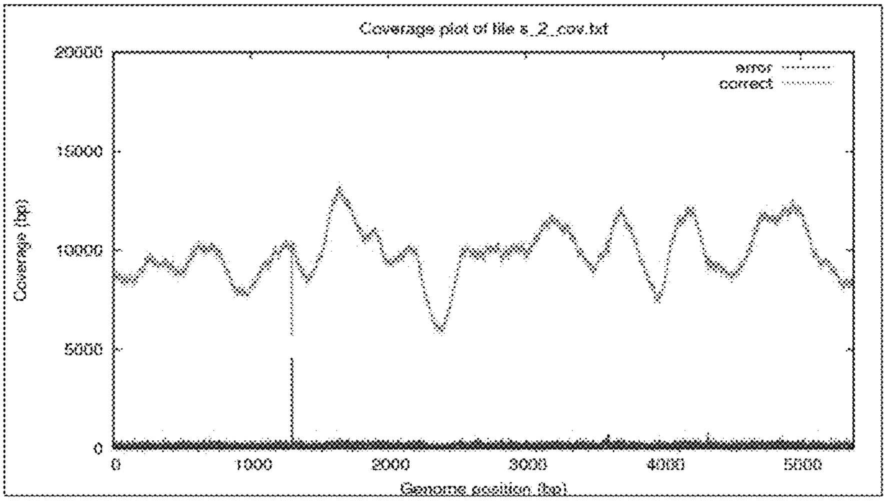
B) Lane 3
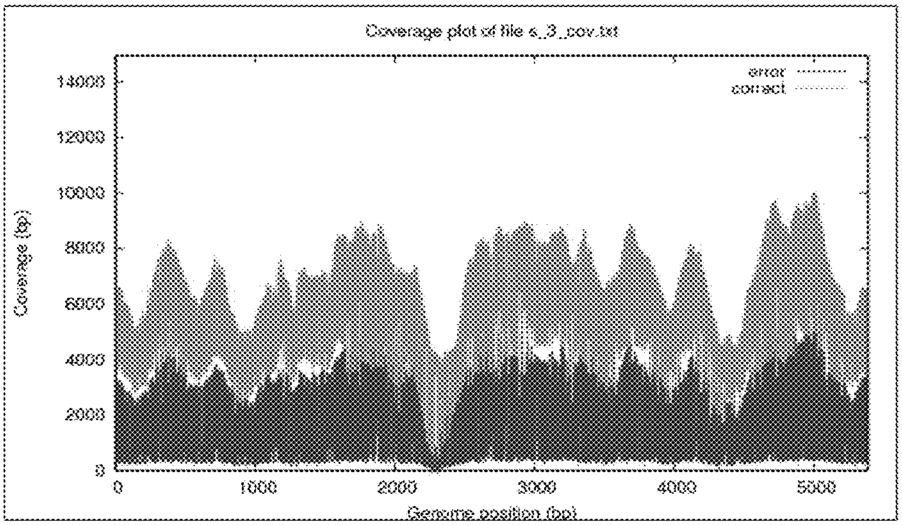

C) Lane 4

FIG. 11
Panel A-Clone A
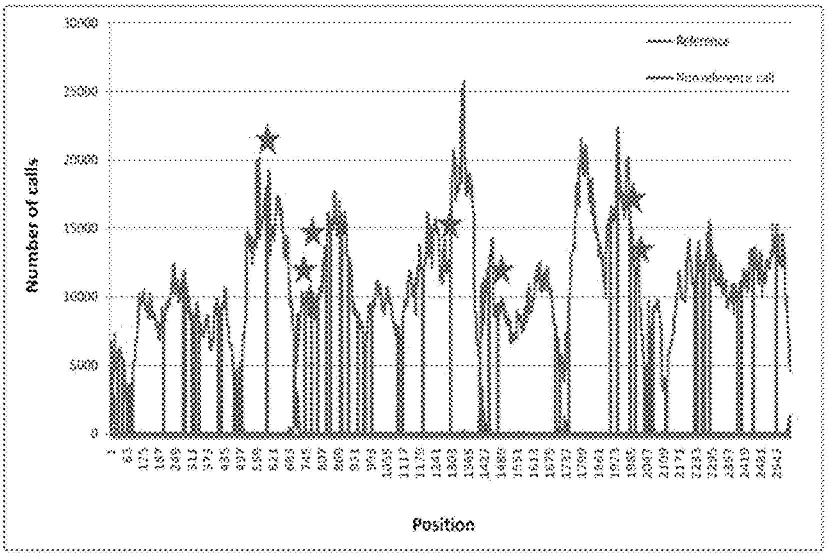
Panel B-Clone B
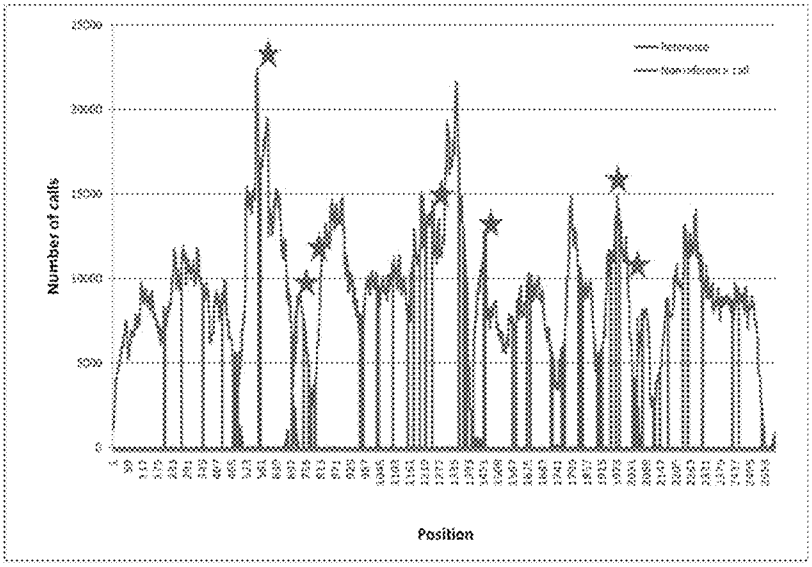

Panel C-Clone D

METHODS AND SYSTEMS FOR DETERMINING HAPLOTYPES AND PHASING OF HAPLOTYPES

The present application claims priority to U.S. Provisional patent application Ser. No. 61/673,052 filed Jul. 18, 2012, which is incorporated herein by reference in its entirety.

BACKGROUND

The efforts of the Human Genome Project opened a broader window to the human genome. The work to further unlock the human genome is ongoing. The HapMap (Haplotype Map) Project is a global scientific effort directed at discovering genetic variants that lead to disease by comparing genomic information from people without a particular disease to those with that disease. Alleles, one or more forms of a DNA sequence for a particular gene, can contain one or more different genetic variants. Identifying haplotypes, or combinations of alleles at different locations, or loci, on a particular chromosome is a main focus of the HapMap Project. Identified haplotypes where the two groups differ might correlate to locations of genetic anomalies that cause disease. As such, HapMap results will help to describe the common patterns of genetic variation in humans and whether those variations are potentially correlated to disease. Research efforts in determining haplotypes will help illuminate the common patterns of genetic variation in humans and whether those variations are potentially correlated to a particular disease. Indeed, many researchers agree that haplotyping a genome will be advantageous, if not essential, in relating genetic variation to phenotype and disease. Further, a particular haplotype may be correlated to the success or failure of a treatment regimen and as such could be useful in helping a clinician decide on a therapeutic regimen for a particular individual that might have the highest degree of success in disease eradication in that individual.

However, there are many technical challenges associated with genomic haplotyping. For example, next generation sequencing technologies while increasing the capacity and accuracy of sequencing efforts, in many cases result in short sequence reads, for example several commercial platforms currently output per fragment reads that are less than 400 nucleotides long. If two or more genetic variants located on a chromosome are further apart than the sequence read length, even if that read length is thousands of base pairs long, it may be difficult if not impossible to define a haplotype. As such, what are needed are methods and compositions that allow for haplotyping, in particular for genetic variants that are farther apart on a chromosome than the sequenced length of a piece of DNA upon which they are found.

BRIEF SUMMARY

Sequencing technologies associated with next generation sequencing can result in short sequence reads thereby making it difficult to determine the haplotype phasing of a genome when the sequences of interest are located far enough apart on the chromosome such that they are outside the window provided by the length of the sequence read.

The present disclosure provides methods and compositions for haplotyping genomic samples and/or determining the phasing of haplotypes using synthetic polymorphisms incorporated into nucleic acids. As described herein, nucleic acid fragments can be modified to convert native nucleotides to synthetic or artificial polymorphisms, such as single nucleotide polymorphisms (SNPs), or other genetic anomalies thereby producing a pattern of engineered polymorphisms in the nucleic acid fragments to be sequenced. After sequencing, the pattern of synthetic polymorphisms can be aligned among the fragments and the haplotype can be determined as a result of the alignment (e.g. haplotype content or phase can be determined). In this manner, a population of modified fragments derived from a genomic sample can be haplotyped even if the alleles for haplotyping lie on different genomic fragments.

Methods and compositions provided herein for creating artificial polymorphisms in a nucleic acid sequence find particular utility for haplotype determination and characterization and/or haplotype phasing; however they can also be advantageous for other purposes. For example, the methods described herein could also be used to facilitate de novo sequence assembly. Further, repeat regions that are nearly identical, for example repeated nucleotide regions such as short tandem repeats, intermediate tandem repeats, etc. as used for forensic DNA fingerprinting could be distinguished from one another by a unique pattern of artificially introduced polymorphisms and thus a more accurate sequence assembly achieved. For example, for forensic sequencing determining the length of a nucleotide repeated region, the order of intermixed repeat regions, and/or the number of repeats (i.e., short tandem repeats, intermediate tandem repeats, etc.) can be performed using the methods herein if the repeated regions are sufficiently long such that they cannot be fully sequenced in a single, or a paired end, sequence read.

Practicing methods disclosed herein for haplotype determination and/or haplotype phasing, de novo sequencing, forensic purposes, etc. can provide critical information useful for, for example, disease and therapeutic regimen correlation. In particular, haplotypes and their phase determinations may become critical in personalized medicine where an individual's haplotype may not only be correlated to a disease, but may also correlate to treatment regimen success and the like for a particular individual.

In one embodiment, the present disclosure provides methods for determining the sequence of a nucleic acid sample comprising providing a plurality of nucleic acid fragments of a first length modified to comprise a plurality of synthetic polymorphisms, preparing a nucleic acid library comprising a second plurality of fragments of nucleic acids of a second length less than that of the first length of fragments from said first plurality of nucleic acid fragments comprising a plurality of synthetic polymorphisms, sequencing said nucleic acid library, and aligning the plurality of synthetic polymorphisms among the sequenced fragments to determine the sequence of the nucleic acid sample based on said alignment. In some instances, the synthetic polymorphisms are a plurality of modified nucleotides that replace the native nucleotides at a particular location and the modified nucleotides are selected from the group consisting of 8-oxoguanine, dPTP, isocytosine and isoguanine. In other instances, modifications to the nucleic acids comprise partial and incomplete bisulfite conversion of cytosines in said plurality of nucleic acid fragments. In some instances, the synthetic polymorphism alignment comprises matching (i.e. by a computer implemented method) a pattern of synthetic polymorphisms in a first nucleic acid fragment sequence with a like pattern of synthetic polymorphisms in a second nucleic acid fragment sequence and repeating said matching with a plurality of nucleic acid fragment sequences thereby creating a sequence alignment based on the plurality of synthetic polymorphisms in a plurality of nucleic acid fragments. In some instances, a nucleic acid library is sequenced using a method selected from the group consisting of sequence by synthesis, sequence by hybridization, sequence by ligation, single molecule sequencing, nanopore sequencing, pyrosequencing and polymerase chain reaction. In some instances, a sequence is determined by fluorescence detection. In preferred instances, the determined sequence comprises one or more haplotypes and further comprises determining the phase of two or more haplotypes in the nucleic acid sample. Oftentimes, the haplotypes for phasing are located on different sequenced fragments. The above disclosed methods could also be used for de novo sequencing.

In another embodiment, the present application discloses a method for characterizing one or more haplotypes of a nucleic acid sample comprising providing a pool of fragmented nucleic acids, introducing a plurality of synthetic polymorphisms such as single nucleotide polymorphisms in the fragmented nucleic acids of said pool to produce fragments comprising a plurality of synthetic polymorphisms, preparing a library of nucleic acid fragments that are shorter in length than the original pool of fragments comprising a plurality of modified nucleic acids, sequencing nucleic acid fragments in the library, aligning the synthetic polymorphisms of the sequenced nucleic acid fragments, and characterizing one or more haplotypes of the nucleic sample from the aligned synthetic polymorphisms of the sequenced fragments. In some instances, the plurality of synthetic single nucleotide polymorphisms replaces the native nucleotides at the site of incorporation and comprises a plurality of modified nucleotides. In some instances, the modified nucleotides are selected from the group consisting of 8-oxoguanine, isocytosine, isoguanine and dPTP. In some instances introduction of the synthetic polymorphisms is accomplished by partial and incomplete bisulfite conversion of cytosines in the nucleic acid fragments. In some instances, the synthetic polymorphisms are aligned by matching (i.e., by a computer implemented program) a pattern of synthetic polymorphisms in a first nucleic acid fragment sequence with a like pattern of synthetic polymorphisms in a second nucleic acid fragment sequence and repeating said matching in a plurality of nucleic acid fragment sequences thereby creating a sequence alignment from the synthetic polymorphisms in the sequenced nucleic acid fragments. In some instances, sequencing is performed by one of sequence by synthesis, sequence by hybridization, sequence by ligation, single molecule sequencing, nanopore sequencing, pyrosequencing and polymerase chain reaction methodologies. In some instances, sequences are determined by fluorescence detection. In some instances, sequences are used to determine the phase of two or more haplotypes in the nucleic acid sample. Oftentimes, the haplotypes for phasing are located on different sequenced fragments. In other instances, the method described above can be used for de novo sequencing.

In another embodiment, the present disclosure describes a method for identifying one or more haplotypes of a nucleic acid sample comprising providing a nucleic acid molecule having a plurality of nucleotides, modifying a plurality of the nucleotides in the nucleic acid molecule, thereby producing a modified nucleic acid molecule comprising natural and modified nucleotides, amplifying the modified nucleic acid molecule to produce a plurality of modified nucleic acid copies of a first length, fragmenting the amplified modified nucleic acid copies under conditions to produce a library of nucleic acid fragments of a second length, wherein individual nucleic acid fragments in the library have a region of sequence overlap with at least one other nucleic acid fragment in the library and wherein the region of sequence overlap comprises at least one modified nucleotide, determining the sequence of nucleic acid fragments of the library, and aligning the sequence of nucleic acid fragments by the locations of the modified nucleotides in the regions of sequence overlap to identify one or more haplotypes of the nucleic acid molecule. In some instances, the nucleic acid molecule comprises several different nucleotide types along the length of sequence and one of the nucleotide types may be modified in the modified nucleic acid or all of the nucleotides of the one type may be modified in the modified nucleic acid. In some instances, only a subset of the nucleotides of the one type is modified in the modified nucleic acid. In some instances, methods for identifying a haplotype further comprises determining the phase for at least two haplotypes in the nucleic acid molecule. Oftentimes the haplotypes for phasing are located on different sequenced fragments. In some instances for haplotyping, the nucleic acid molecule comprises several different nucleotide types along the length of sequence, wherein the at least two haplotypes are bi-allelic for two of the nucleotide types, and wherein a third nucleotide type is modified in the modified nucleic acid. In other instances, at least two haplotypes are bi-allelic for nucleotide types that are selected from the group consisting of A, T and G, and wherein C is modified to U in the modified nucleic acid. In other instances, at least two haplotypes are bi-allelic for T and G, and wherein C is modified to U in the modified nucleic acid. In additional embodiments, at least two haplotypes are bi-allelic for nucleotide types that are selected from the group consisting of A, T and C, and wherein G is modified to 8-oxo-G in the modified nucleic acid. In other instances, at least two haplotypes are bi-allelic for C and T, and further G is modified to 8-oxo-G in the modified nucleic acid.

DESCRIPTION OF THE DRAWINGS

FIG. 4 demonstrates an embodiment where the target DNA contains artificial polymorphisms created using sodium bisulfite conversion methodology. The natural occurring SNPs (bolded and enlarged) on A) allele 1 G and C and B) allele 2 T and A are separated by a distance greater than a typical insert library size and therefore the SNP phasing is indeterminable, whereas artificial C to T polymorphisms which can be incorporated in the nucleic acid by partial bisulfite conversion can be used to align sequenced fragments so that a haplotype can be determined for the two alleles.

FIG. 7 shows sequencing data for the percent of modified nucleotides (% error rates) incorporated into phiX template DNA extension products for flowcell lanes 1, 2, 3 and 4.

FIG. 8 shows sequencing data for the percent of phiX sequencing reads by cycle having 0, <1, <2, <3 or <4 incorporated modified nucleotides. Y axis is % reads with X errors or less 0-100%, X axis is cycle number 0-100.

DETAILED DESCRIPTION

Figure 1:
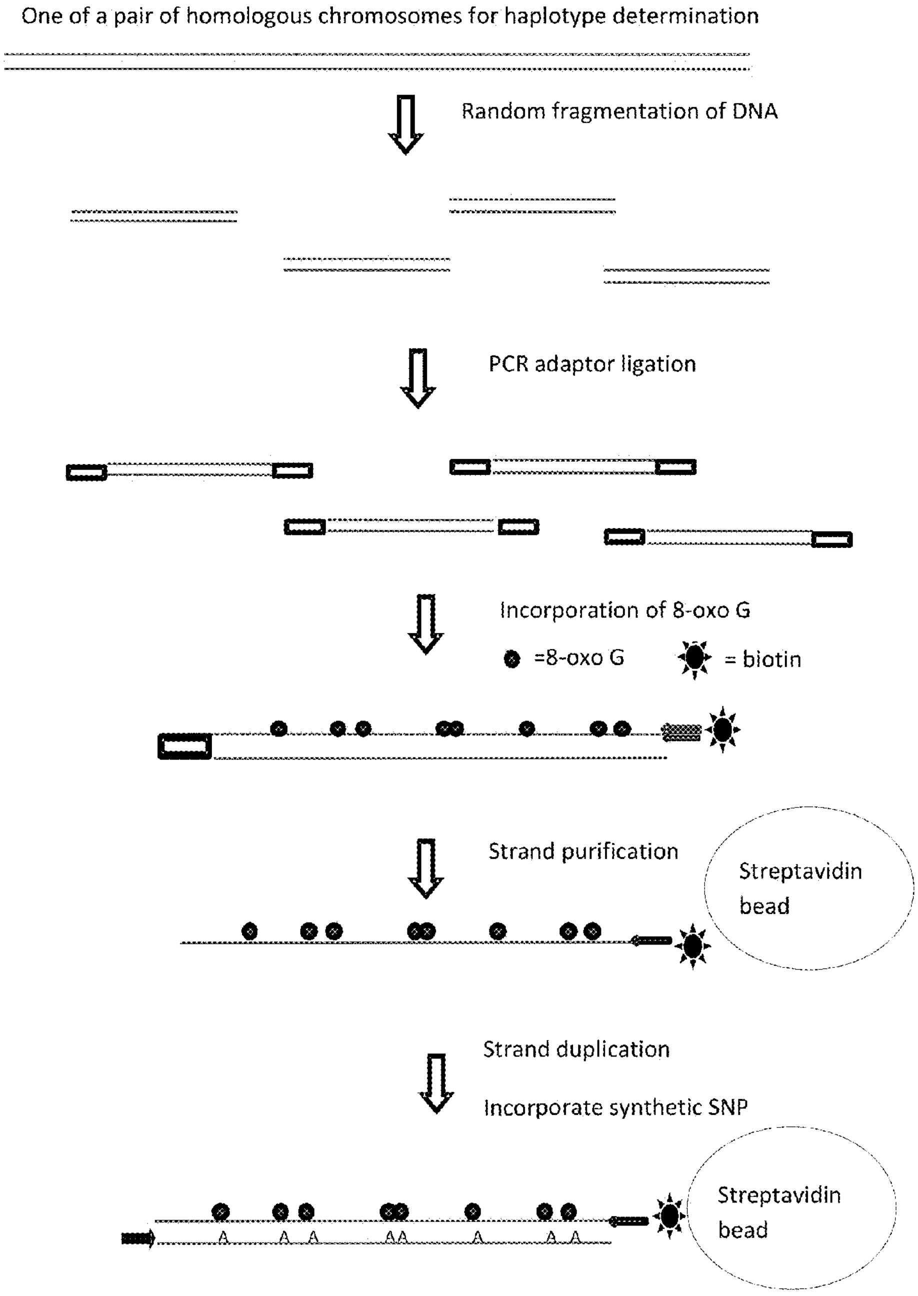
FIG. 1 shows an embodiment for incorporating the modified nucleotide 8-oxoguanine (8-oxo G) into DNA thereby converting natural nucleotides in a sequence to synthetic polymorphisms in a sequence.
Figure 1:
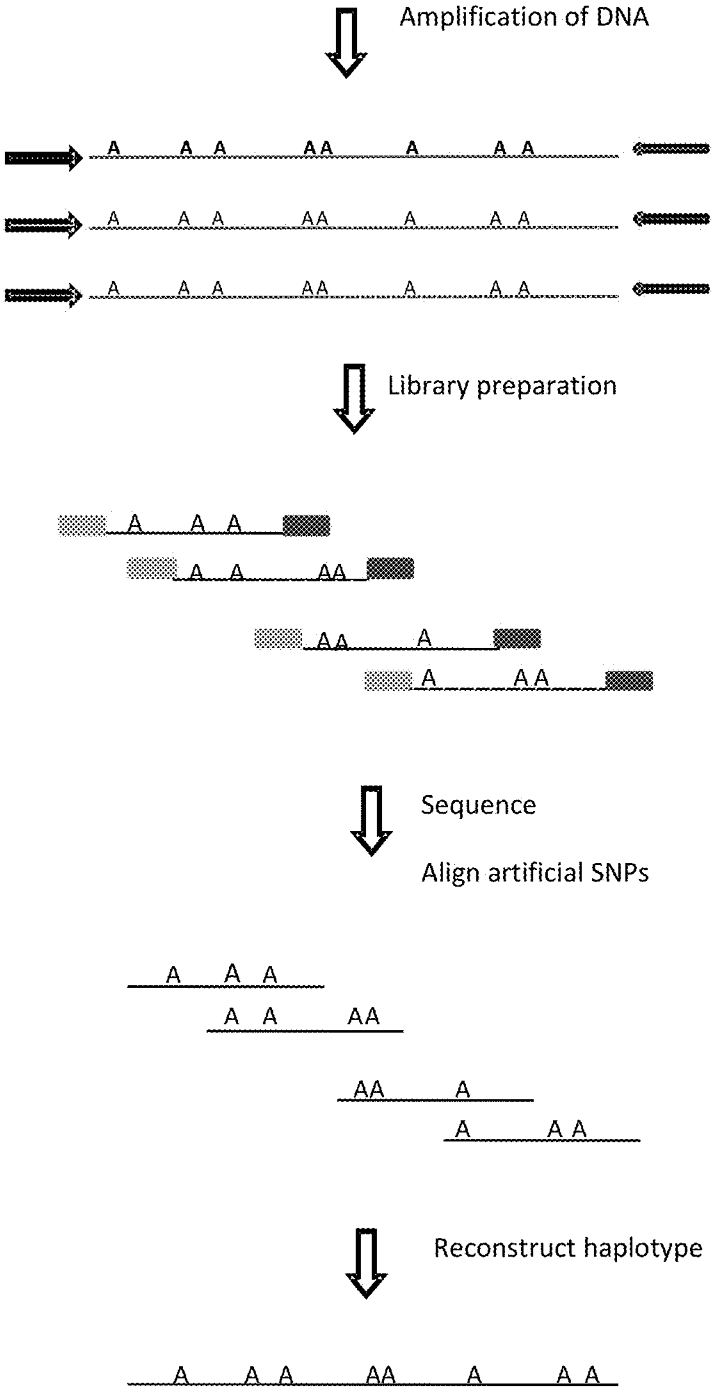

The ability to determine groups of closely linked alleles in a genome that are inherited together, or haplotyping, may help to map human disease genes. Disease maps could be used to diagnose, prognose and/or identify disease or risk of disease for a patient as well as determine potential treatment therapies unique to any one person. Such is one of the goals of personalized healthcare. However, the same holds true for plant and animal species, for example economically relevant plant and animal species, wherein sequence knowledge such as haplotyping could also be used to advantage in veterinary and plant sciences. As such, determining a haplotype and/or phasing of haplotypes is important from both a biological and clinical point of view. Sequencing a sample provides sequence information with which an investigator can start to unravel and determine such correlations.

As used herein, the term "haplotype" refers to a haploid genotype, a combination or set of alleles or DNA sequences found at different locations or loci on a chromosome which are typically inherited as a unit and are linked, for example during a recombination event. A haplotype can provide a distinctive genetic pattern of an individual. A haplotype can be determined for one locus, several loci, over a portion of or for an entire chromosome. The term "allele" is used consistent with its meaning in the art of biology. An allele is one or more alternative forms of a gene, genetic sequence or single nucleotide (e.g. a single nucleotide polymorphism or SNP) found at a specific location, or locus, on a chromosome. The term "locus" is used consistent with its meaning in the art of biology. A locus (plural "loci") refers to a specific location or place on a chromosome identified with a gene, genetic sequence or single nucleotide. As such, one or more alleles for a particular gene, for example, can be found at a particular locus on a chromosome. Different genes can be identified with different loci on a chromosome, wherein each gene, for example, may be associated with one or more different allelic sequences. Alleles are not limited to any specific type and may include, for example, normal genetic sequences or variant genetic sequences. For example, single nucleotide polymorphisms (SNPs), short tandem repeats (STRs), etc. can be included as variants and genetic sequences. The term "phased alleles" refers to the distribution of the particular alleles on a chromosome. Accordingly, the "phase" of two alleles can refer to a characterization or determination of whether the alleles are located on a single chromosome or two separate chromosomes (e.g. a maternally or paternally inherited chromosome).

Even though sequencing technologies can produce a very large number of sequence reads, the read lengths can be relatively short. While next-generation sequencing technology may increase the accuracy of sequencing and may be useful for calling variants, the technology can be of limited use when phase, or haplotype information, is desired. Phasing information derived from short sequence reads have previously been very difficult to determine unless the two polymorphisms of interest were so close to one another that they were present on the same sequenced fragment of DNA, or perhaps in a case where one polymorphism was determined to be present from a first sequence read and the second polymorphism was detected in the second sequence read of the same pair of nucleic acid fragments. Instances resulting from the second case are contemplated to be rare since, on average, the human genome has one polymorphism for every 1000 nucleotides. As such, the probability of a particular read containing a polymorphism may be approximately 15% (sequence read length/polymorphism frequency of one polymorphism every 1000 nucleotides). The combined probability of both reads belonging to a pair of sequences having each one polymorphism is the product of the individual probabilities (15%×15%). Therefore, it is contemplated that a small subset of fragment read pairs, for example approximately 2.25% of short fragment read pairs, could contain two variant sequences that form a haplotype. This is further complicated when taking into account that the average insert size distribution of the typical sequencing library, for example a library created for a next generation sequencing technology can range from approximately <50 bp (e.g., Life Technologies SOLiD sequencing at mate paired sequencing) to approximately <400 bp (e.g., 454 Life Sciences GS FLX Titanium sequencing). As such, if two polymorphisms are at a distance of, for example, >400 bp from one another, the likelihood of being linked by paired reads derived from a library is practically zero. The same is true for reads longer than 400 bp as it is assumed that sequencing reads may increase in length in the future, however the disclosed methods would still be applicable as, if two polymorphisms are at a greater distance than the sequence read the current methods could be utilized to determine a haplotype from polymorphisms located on separate reads.

The present disclosure provides solutions for characterizing genomic haplotypes (e.g. haplotype content or phase) which are particularly useful when dealing with short read length sequence information. The present disclosure provides methods and compositions for enabling haplotype characterization from sequence information, in particular when the alleles of interest are located on different sequenced nucleic acid fragments.

Embodiments herein disclose methods for creating "artificial polymorphisms" or "synthetic polymorphisms" such as artificial or synthetic single nucleotide polymorphisms or "artificial SNPs" ("synthetic SNPs") which can be incorporated into nucleic acids prior to sequencing such as by replacing a native nucleotide with a modified nucleotide, or by converting one nucleotide to another through bisulfite conversion. As used herein, the terms "synthetic polymorphism" or "artificial polymorphism", are synonymous unless otherwise stated. Synthetic or artificial polymorphisms represent sequences in a nucleic acid sample that are not naturally occurring in the nucleic acid sample, but instead are incorporated by methodological means into the nucleic acid sample. The synthetic polymorphism could be inserted into the sequence of a genome, or the synthetic polymorphism could replace a sequence of the nucleic acid sample. Examples of synthetic polymorphisms include, but are not limited to, single nucleotide polymorphisms (i.e., artificial or synthetic SNPs), dinucleotide polymorphisms, insertions of nucleic acids (e.g., one or more nucleic acids, etc.) and deletions of nucleic acids (e.g., one or more nucleic acids, etc.). The artificial sequences for incorporation into a natural nucleic acid or polynucleotide sample comprise modified nucleotides including, but not limited to, 2-thio thymidine triphosphate, 5-(2'-deoxy-D-ribofuranosyl)-3-methyl-2-pyridone-5' triphosphate, 8-oxoguanine (8-hydroxyguanine, 8-oxo-7,8-dihydroguanine or 2-amino-7,9-dihydro-1H-purine-6,8-dione), 8-Oxo-2'-deoxyguanosine-5'-triphosphate, 2'-Deoxy-P-nucleoside-5' triphosphate (dPTP), $d^{5m}$CTP for example, m7G(5')ppp(5'); P1-5'-(7-Methyl)-guanosine-P3-5''-guanosine triphosphate, methyl5-dCTP, hydroxymethyl dCTP, isocytosine, isoguanine, and derivatives thereof, to name but a few.

The artificial or synthetic polymorphisms can be incorporated, for example, at a certain frequency such that they can be aligned and phased even from short sequence reads or pairs of reads. In one embodiment, a method for creating artificial polymorphisms in a nucleic acid strand comprises incorporating a plurality of nucleic acid analogs, for example a guanine analog such as 8-oxoguanine (8-oxo G), into a nucleic acid strand. The amount of modified nucleotide 8-oxoguanine (8-hydroxyguanine, 8-oxo-7,8-dihydroguanine or 2-amino-7,9-dihydro-1H-purine-6,8-dione (IUPAC)) found normally in mammalian DNA increases in DNA, for example that is damaged due to oxidative damage caused by oxygen free radical species and/or ionizing radiation (1992, Cheng et al., J Biol Chem 267:166-172, incorporated herein by reference in its entirety). During replication, 8-oxo G can base pair to either a cytosine (C) and/or adenine (A) via Hoogsteen base pairing (LePage et al., Nucl Acids Res, 1998, 26:1276-1281, incorporated herein by reference in its entirety). The 8-oxo G (e.g., by incorporation during an extension reaction of 8-Oxo-2'-deoxyguanosine-5'-triphosphate or 8OxodGTP) can be incorporated into a polynucleotide by a variety of means, for example by ionizing radiation or another means of oxidatively stressing the cellular DNA. Alternatively, the modified nucleotide can be added to a dNTP mix and, during an extension reaction of one or both strands of a polynucleotide can be incorporated into an extended DNA strand thereby replacing the normally incorporated non-modified nucleotide at a certain frequency. Following incorporation of the 8-oxo G into a strand of the polynucleotide, adenine mispairing can be accomplished during a DNA replication step by pairing of an adenine in the replicating strand opposite the 8-oxo G in the parent strand.

In one embodiment, 8-oxo G can be incorporated into a polynucleotide prior to library preparation for sequencing. For example, a genomic DNA sample can be fragmented, the fragment ends repaired, adenines added to the ends via A-tailing and primer adaptors added to the ends for replication and amplification, for example. During replication of the fragments 8OxodGTP can be added along with a canonical dNTP mix (dATP, dTTP, dGTP and dCTP) which would result in the replacement of a plurality of guanines with a plurality of 8-oxo G guanine analogs into the DNA fragment in a random fashion. The percent of 8OxodGTP can be empirically determined. In some embodiments, the percent of 8OxodGTP is at least 10%, at least 20%, at least 30%, at least 30%, at least 50%, at least 60%, at least 70%, at least 80% at least 90% or at least 100% of guanines (e.g., as a replacement for dGTP) available for incorporation during fragment replication. The percentage, and therefore ratio, of guanine analog compared to the canonical dGTP can be empirically determined for the amount of replacement desired by the user. It will be understood that similar percentages or ratios can be used for other nucleotides (or modified nucleotides) that are incorporated into nucleic acids using methods and compositions set forth herein, for example, in order to introduce artificial SNPs. Continuing with the example of 8-oxo G, the genomic fragments containing 8-oxo G can be subsequently isolated from those fragments that lack 8-oxo G. Isolation of the 8-oxo G containing fragment can be by any means. For example, a primer used during replication could be complexed with a binding molecule that binds a binding partner for isolation purposes. Such binding partner pairs include, but are not limited to, haptens, small molecules, dyes and antibodies such as for example biotin/streptavidin, biotin/avidin, biotin/neutravidin, DNP/anti-DNP, DIG/anti-DIG, etc. Isolation of 8-oxo G containing DNA can also be isolated by capture with an 8-oxo G specific antibody such as Oxoguanine 8 antibody [2Q2311] (ab64548 from AbCam). The 8-oxo G containing DNA can also be eliminated from downstream haplotyping methods by either denaturation and washing or digestion for example with formamidopyrimidine DNA glycosylase (Fpg) (also known as 8-Oxoguanine DNA glycosylase, NEB).

FIG. 1 exemplifies an embodiment using 8OxodGTP in methods for incorporating synthetic polymorphisms into genomic DNA. In FIG. 1, genomic DNA can be randomly fragmented into large fragments. The size of the initial large fragments can be at least 500 bp, at least 750 bp, at least 1000 bp, at least 1500 bp, at least 2000 bp, at least 3000 bp, at least 4000 bp, at least 5000 bp. The size of the initial fragments can be determined empirically and may vary between different regions of the genome that have different frequencies of guanines which would affect the amount of downstream guanine analog incorporation. Fragmentation can be by any means, for example sonication, Hydroshearing, nebulization, mechanical shearing and transposon methodologies, etc. The fragments can be end repaired, A-tailed and adaptor ligated. The nucleotide 8-oxo G can be incorporated into a strand of the genomic fragment by primer extension and a dNTP mix that includes 8OxodGTP. The primer utilized for DNA extension and incorporation of the modified nucleotide can be complexed with biotin which can be subsequently captured by a streptavidin molecule for isolation of the 8-oxo G containing strand. The captured 8-oxo G containing templates can be replicated resulting in 8-oxo G mispairs with adenines, thereby creating double stranded DNA molecules wherein the template contains the guanine analogs and the copied strand contains the mispaired adenines. To remove the 8-oxo G containing strands, thereby leaving the adenine containing strands, the primer used for replication of the second strand can be affixed to a capture moiety such as biotin and capture by streptavidin can be performed.

The remaining adenine containing polynucleotides can be further amplified and processed to create a library of fragments for sequencing. The created synthetic adenine SNPs in the fragments are random and, due to the randomness of the guanine substitutions with 8-oxo G, the pattern of introduced synthetic SNPs can be used to uniquely identify the parental fragments. Following sequencing the artificial SNP patterns can be aligned among all the fragments thereby combining the fragment sequences in the original genomic order for haplotype determination, such as determination of haplotype content or phase.

In another embodiment, a method for introducing artificial polymorphisms in a genomic DNA for sequencing comprises modifying DNA with bisulfite thereby creating a pattern of artificial polymorphisms. In one example, applying bisulfite to a nucleic acid sample in low concentration or for a short period of time can modify DNA by incompletely and partially converting a subset of unmethylated cytosine residues to uracils and uracils into thymines thereafter to create artificial thymine polymorphisms at a plurality of locations in the genomic DNA. When mammalian DNA is treated with bisulfite, methylated cytosines (e.g., 5-methylcytosine) remain untouched whereas cytosine residues that are not methylated are converted to uracils. Therefore, by utilizing the methylation status of a genomic DNA sample and treating genomic DNA with bisulfite a pattern of artificial T SNPs (C to U to T) can be created which can be aligned among the fragments after sequencing to reconstruct the genomic DNA chromosomal sequence for subsequent haplotype characterization (e.g. identification of the haplotype content or phase). In preferred embodiments, partial and incomplete conversion of methylated cytosine residues is preferred when practicing methods disclosed herein for creating a pattern of synthetic polymorphisms in a polynucleotide.

Examples of natural cytosine sequence configurations which could be targets for partial bisulfite conversion include, but are not limited to CG methylation dinucleotides (1994, Clark et al., Nucl Acids Res 22:2990-2997, incorporated herein by reference in its entirety), CpT and CpA dinucleotide regions (2000, Lyko et al., Nature 408:538-540; 2000, Ramsahoye et al., Proc Nat Acad Sci 97:5237-5242; 2001, Haines et al., Dev Biol 240:585-598, incorporated herein by reference in their entireties) and CHG and CHH in stem cells wherein H can be either an adenine (A), cytosine (C) or thymine (T) (2009, Lister et al., Nature 462:315-322, incorporated herein by reference in its entirety).

An amplification step can be utilized to create multiple copies of each parental fragment with the newly integrated artificial SNPs prior to library preparation. As such, differences between methylation patterns found on maternal and paternal chromosomes could be exploited by following the methods disclosed herein.

In other embodiments, DNA can be modified in vitro to include methylated nucleotides (e.g., modified nucleotides which are non-native methylated nucleotides). For example, methylated nucleotides can be incorporated into a plurality of locations in a polynucleotide by amplification, such as amplification of a nucleic acid in the presence of canonical dNTPs wherein one of the dNTPs is replaced in whole, preferentially in part, with a methylated dNTP including, but not limited to, $d^{5m}$CTP, m7G(5')ppp(5'); P1-5'-(7-Methyl)-guanosine-P3-5"-guanosine triphosphate (Roche Applied Science), methyl5-dCTP (Zymo Research), or hydroxymethyl dCTP (Bioline). Additionally, methylated dNTPs can be spiked into an amplification reaction in a background of canonical dNTPs. Partial bisulfite conversion could then be carried out on the in vitro modified DNA as described herein for creating a pattern of synthetic polymorphisms in a nucleic acid sample.

Figure 2:
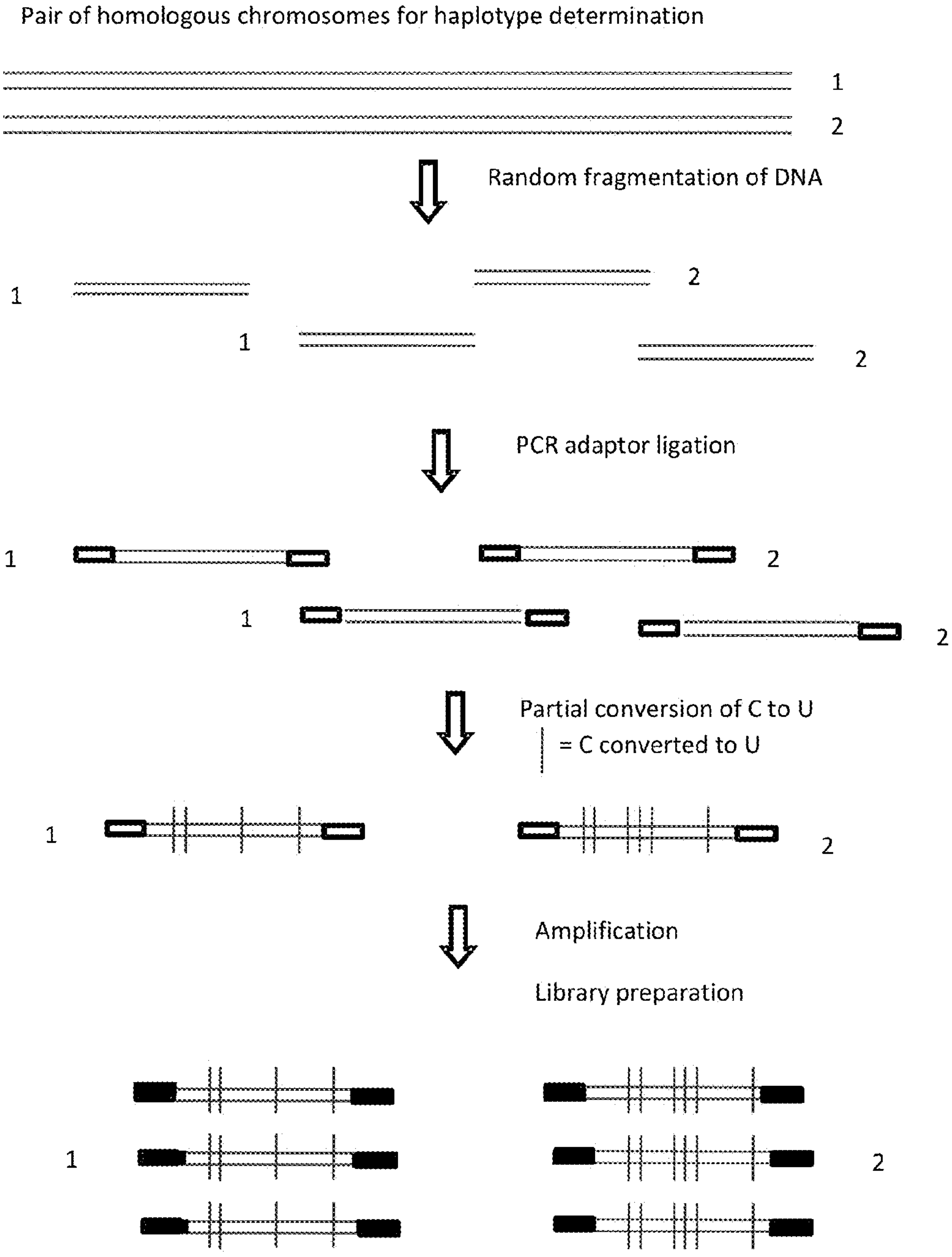
FIG. 2 shows an embodiment for incorporating synthetic polymorphisms into a polynucleotide by partial sodium bisulfite conversion of cytosines to uracils in DNA.
Figure 2:
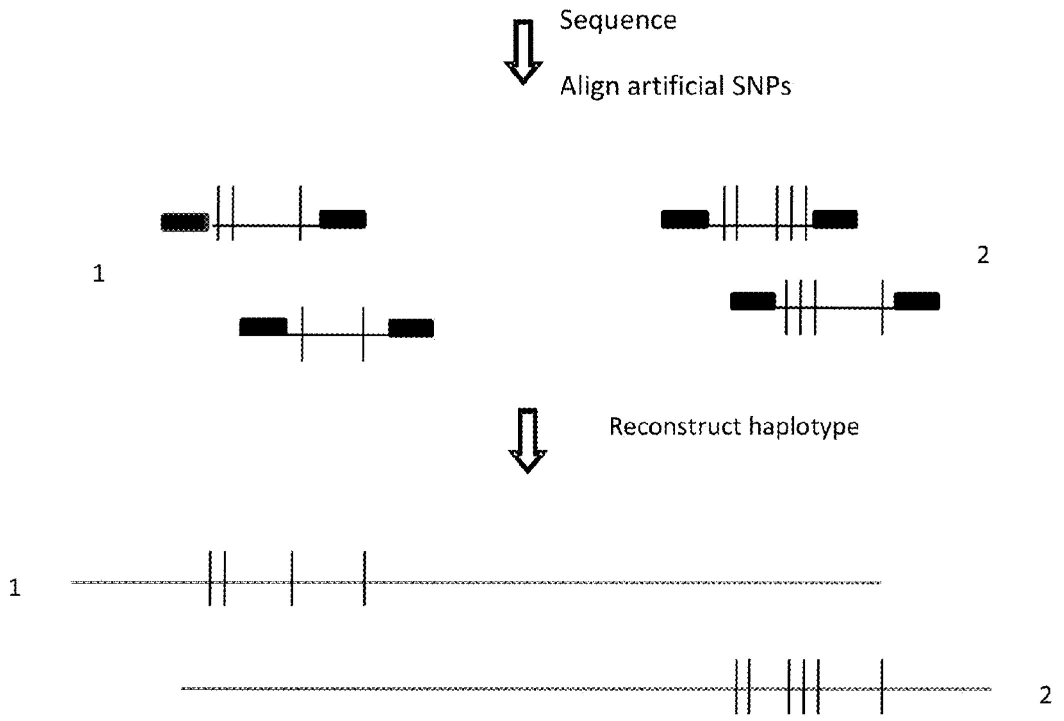

The use of natural methylation status of a genomic DNA sample to create artificial SNPs for haplotyping and/or haplotype phasing determination is exemplified in FIG. 2. In FIG. 2, genomic DNA is fragmented as previously described and the fragment ends are repaired and A-tailed using methods known in the art (for example, see Molecular Cloning; A Laboratory Manual, Eds. Sambrook, Fritsch and Maniatus, Cold Spring Harbor Laboratory Press) as previously exemplified in FIG. 1. The prepared genomic fragments can be ligated to adaptors for subsequent amplification of the fragments. The adaptors for use with the bisulfite conversion method for creating artificial SNPs can be designed so that they are extendable and amplifiable following bisulfite treatment. For example, the adaptors can be pre-methylated (i.e., methylated adaptors), or adaptors could be designed which lack cytosine nucleotides where primer binding occurs. The adaptor ligated fragments can be amplified and copied using dTTP to replace the uracils prior to library preparation. Following library preparation and sequencing the artificial SNP patterns in the fragmented sequences can be aligned to reconstruct the original genomic DNA which can then be haplotyped. The partial conversion of cytosines by bisulfite conversion creates synthetic SNPs in the fragments wherein, due to the randomness of the conversions, the pattern of synthetic SNPs can be used to uniquely identify the parental fragments.

Alternatively, in some embodiments the partial conversion of cytosines to uracils can be performed prior to genomic DNA fragmentation and/or adaptor ligation, in which case the ligated adapters need not be methylated or otherwise designed to resist bisulfite treatment of cytosines.

In another embodiment, methods for determining haplotype of a genomic sequence comprise the use of modified nucleotides such as isoC and isoG. Isocytosine (isoC, iC) and isoguanine (isoG, iG), modified nucleotides having the amine and ketone groups inverted as compared to the standard cytosine and guanine nucleotides, can be misincorporated into a DNA strand resulting in the random placement of artificial polymorphisms. In the case of isoC and isoG, the polymorphisms created can be copied or sequenced in later steps using the correct complementary non-natural partner. In this embodiment, it is advantageous to misincorporate the isoC and isoG in the initial DNA replication step and change conditions for subsequent amplification steps (i.e., such as those used in library preparation methods) to minimize or preferentially stop further misincorporation (2005, Sismour and Benner, Nucl Acids Res 33:5640-5646, incorporated herein by reference in its entirety) to faithfully copy the newly formed artificial polymorphisms.

Figure 3:
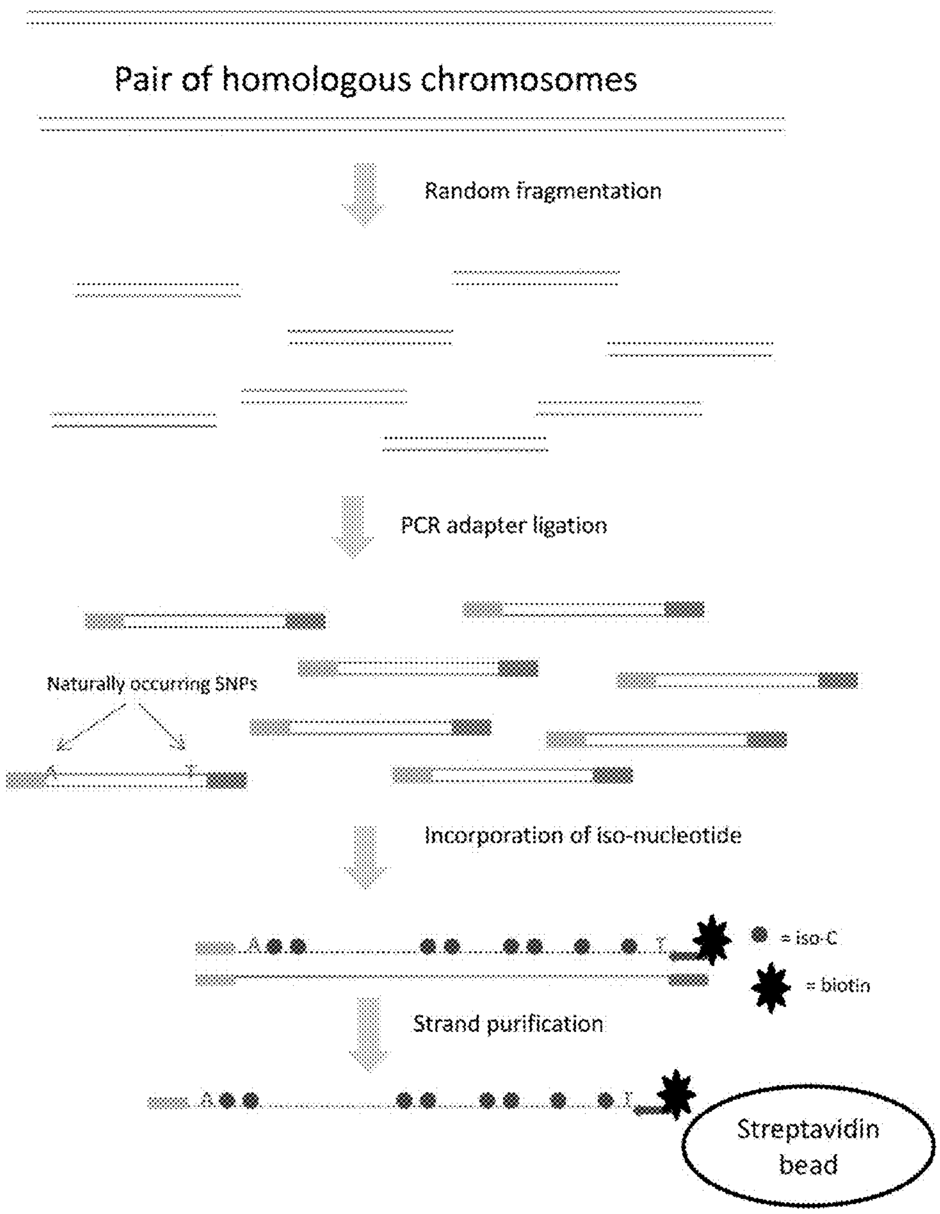
FIG. 3 depicts an embodiment for incorporating synthetic polymorphisms into a polynucleotide by incorporating the modified nucleotides isocytosine and isoguanine into DNA in lieu of the native nucleotides.
Figure 3:
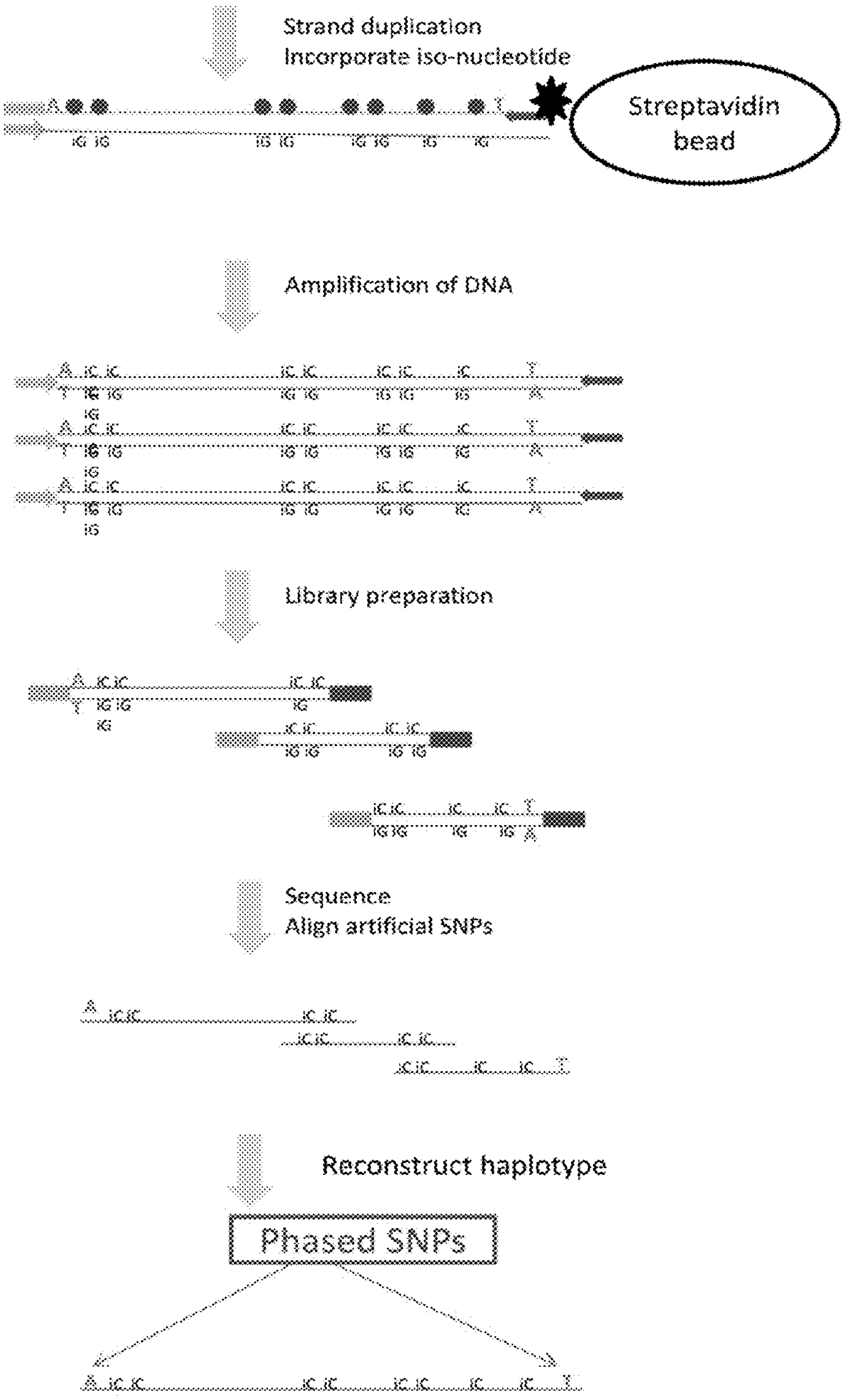

FIG. 3 is exemplary of the use of modified nucleotides in methods for creating artificial polymorphisms in DNA. For example, genomic DNA can be fragmented as previously described. Adaptors can be ligated to the ends of the random fragments as previously described. Exemplary naturally occurring SNPs A and T are depicted on one of the fragments; these SNPs being targeted as an example for haplotyping. During extension, a modified nucleotide, in this example iC, can be incorporated into the extended strand which is further end labeled with a binding moiety affixed to the extension primer, in this example biotin. The modified nucleotide deoxyisocytosine diCTP can be part of the extension dNTP mix in a defined ratio or percentage. Such ratios or percentages can be determined empirically for the amount of synthetic polymorphism incorporation desired by an investigator. The strand comprising the modified nucleotide can be captured with the binding partner, in this case streptavidin and subsequent strand duplication can incorporate the mate to the modified nucleotide, in this case iG as described for iC. The double stranded fragments, which comprise iC on one strand and iG on the other can be amplified thereby creating multiple fragments comprising both modified nucleotides for use in library preparation.

Figure 6:
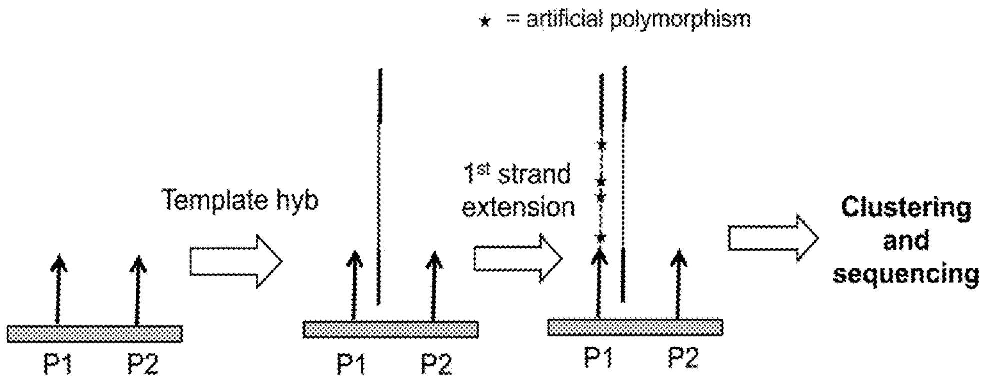
FIG. 6 shows an example of how the embodiment for a "first strand extension reaction" can be used to incorporate synthetic polymorphisms into a DNA target.

In another embodiment, synthetic polymorphisms can alternatively be incorporated into genomic library fragments downstream of fragment library preparation. For example, once the genomic library is created (by any means known to a skilled artisan, for example as discussed herein), synthetic polymorphisms can be incorporated in steps between the library preparation and sequencing. In one non-limiting example, synthetic polymorphisms can be incorporated during colony formation prior to sequence by synthesis methodologies. In this case, the DNA library can be hybridized to primers affixed on a substrate and a first strand extension reaction can be utilized to incorporate modified nucleotides into the fragment library. This “first strand extension reaction” format is exemplified in FIG. 6. Briefly, two primers (P1 and P2) which are homologous to primers affixed to the ends of the DNA library fragments are bound to locations on a substrate such as a flowcell (e.g., lanes or wells on a flowcell), wells, plates, and the like. The template DNA library fragments can be hybridized to the substrate bound primers and a complementary DNA strand can be synthesized (e.g., $1^{st}$ strand extension on FIG. 6) in the presence of modified nucleotides. Clustering, sequencing and aligning can be performed to align the incorporated artificial polymorphisms to provide a sequence useful for haplotype determination.

For all embodiments described herein for incorporating artificial polymorphisms into genomic DNA for sequencing, libraries for sequencing can be prepared using a method compatible with the downstream sequencing instrument. The sequences of fragments, once determined, can be aligned on the basis of the synthetic SNPs present in the fragments and a haplotype can be constructed and determined based on that alignment, for example when the length of the sequence read is shorter than the distance between the two alleles for haplotype determination.

The first sequences in FIGS. 4 A and B shows two exemplary alleles (allele 1 and 2) comprising naturally occurring polymorphisms, in this example SNPs, which are separated by more than 400 nucleotides (G-C in allele 1 and T-A in allele 2). As the distance between these SNPs is greater than the average insert size of the library preparatory method for sequencing, phasing or haplotyping of the two SNPs would not be determinable using unmodified nucleotides. The second sequences in FIGS. 4 A and B show the same region from exemplary alleles 1 and 2 after practicing a method of the present disclosure, for example practicing the method of partial bisulfite conversion of the parental genomic fragments prior to sequencing. The two modified allelic sequences demonstrate an example of a unique pattern of artificial polymorphisms which could be created by bisulfite conversion as disclosed herein.

Figure 5:
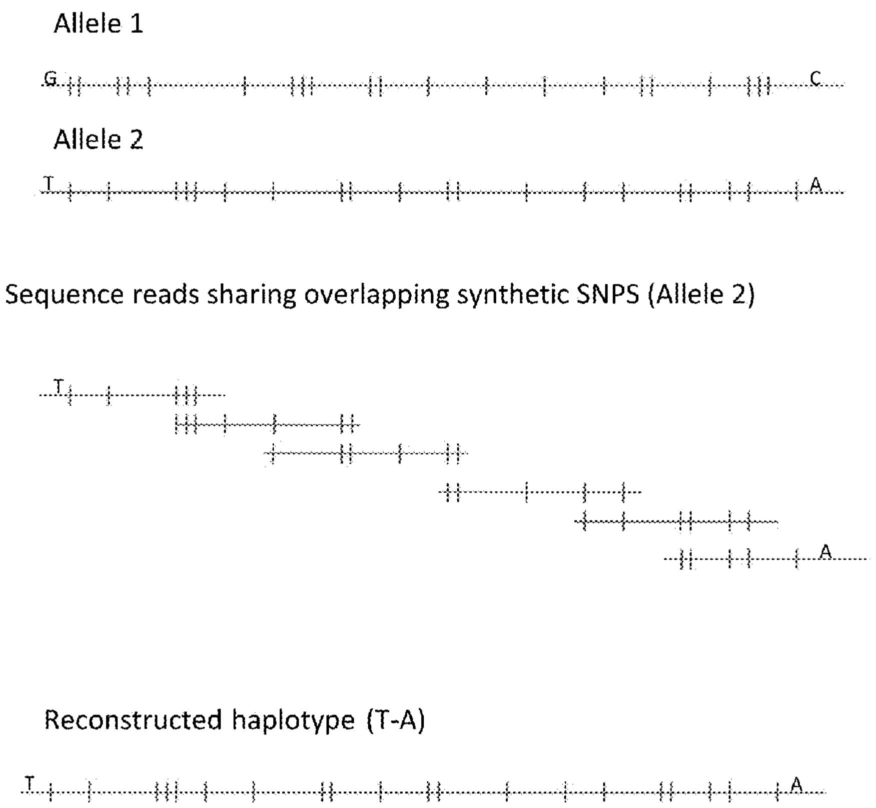
FIG. 5 shows an example of haplotype reconstruction. The incorporated artificial SNPs are depicted as vertical lines on the linear DNA fragments Allele 1 and Allele 2. The DNA is fragmented, sequenced and the sequencing reads are aligned based on the unique pattern of the incorporated synthetic SNPs (allele 2 from FIG. 4 depicted in this Figure). The alignment of the artificial SNPs in the overlapping fragments allows for the rebuilding of the original genomic fragment sequence and the reconstruction of the haplotype for allele 2 can be determined.

After sequencing, the short length sequence reads would be aligned based on the artificial polymorphisms to recreate the unique pattern for each allele, thereby reconstructing the original genomic DNA fragment (FIG. 5). The haplotype reconstruction of the two alleles, using allele 2 in FIG. 5, is determined following fragment alignment based on synthetic polymorphic patterns. As such, incorporating synthetic polymorphisms into a nucleic acid molecule prior to sequencing allows for a unique synthetic pattern which can be subsequently aligned post sequencing among the different sequence fragments, thereby providing a means for bridging the distance between the naturally occurring SNPs to determine their haplotype content or phase.

Additionally, methods disclosed herein provide a means for determining the origin of the sequenced fragments. For example, the relative frequency of artificial polymorphism creation and their random nature enables the determination of whether or not two DNA sequencing populations (e.g., two or more DNA clusters, isolated populations of DNA amplicons derived from one template, etc.) are derived from the same original parental DNA molecule. If two or more populations share the same overlapping pattern of artificial polymorphisms, it is contemplated that they are derived from the same chromosome and therefore all of the natural SNPs present in the populations can be haplotypes or phased together.

Therefore, the methods of creating artificial polymorphisms in a target genomic sequence which are designed to occur at a much higher frequency (or in closer proximity) in the target genomic DNA compared to the frequency (or proximity) of naturally occurring SNPs can be exploited to link naturally occurring SNPs in a target sequence when it was not previously possible due to the distance of separation between the naturally occurring SNPs in the target relative to the sequence read length. Moreover, embodiments for creating artificial polymorphisms in a target genomic DNA as disclosed herein require no prior knowledge of the sequence being haplotyped. Although the creation of artificial polymorphisms does fundamentally change the sequence being evaluated, it is possible to remove the artificial polymorphisms from the final consensus sequence of a region by either comparing to a $2^{nd}$ library with no artificial polymorphisms, or by ignoring the artificial positions and using sequence data from other fragments to cover those bases (for example, an artificial polymorphism can be identified and ignored if it occurs in for example 5-10% of fragments covering a particular position).

In another embodiment, methods for determining a haplotype of a nucleic acid sample comprise incorporating artificial polymorphisms into the nucleic acid by biased amplification. Exemplary methods for performing biased amplification can be found at, for example, WO2011/106368 (incorporated herein by reference in its entirety). Biased amplification (i.e., the process of increasing the numbers of a polynucleotide which can be linear or exponential) may comprise amplifying the target sequences wherein said amplification results in a deoxyribonucleotide triphosphate (dNTP) being incorporated into the nucleic acid strand at a lower efficiency compared to another nucleotide. The methods may use a pool of dNTPs, wherein not all of the dNTPs (i.e., dATP, dTTP, dCTP, dGTP) are present at the same concentration in the pool. Pools of nucleotides may also include modified nucleotides such as those previously mentioned, which incorporate less efficiently (or less often) than canonical nucleotides.

For example, one or more of the dNTPs may be present at a concentration that is less than half of the combined concentrations of any other nucleotide in a step carried out in a method set forth herein such as an amplification reaction step. The concentration of any one type of dNTP may be, for example, less than ¼ the concentration of the other combined nucleotides, less than ⅕ the concentration of the other combined nucleotides, less than 1/10 the concentration of the other combined nucleotides, etc. Alternatively, the concentration of a particular type of dNTP in an amplification reaction may be less than 20 uM, less than 10 uM, less than 0.2 uM compared to the concentration of the remaining dNTPs (e.g., 200 uM) present for an amplification reaction. Alternatively, the concentration of a particular type of dNTP in a composition or method set forth herein could be at least 5 fold less, at least 10 fold less, at least 20 fold less, at least 50 fold less than the concentration of the remaining dNTPs that are present. In such a biased mixture, one or more adjuvants may be added. For example, ethylene glycol, polyethylene glycol, 1,2-propanediol, dimethyl sulfoxide, glycerol, formamide, 7-deaza-GTP, acetamide, tetramethyl ammonium chloride, salt or carboxymethyl trimethyl ammonium. Concentrations of the one or more adjuvants may be between, for example, 2 to 5M. A skilled artisan will understand that conditions may vary from reaction to reaction; as such some optimization for any particular system is contemplated (for example, amplification reaction conditions can be optimized in accordance with WO2011/106368, which is incorporated herein by reference in its entirety).

It is contemplated that incorporating the synthetic polymorphisms as described herein into target nucleic acids of interest prior to library preparation is advantageous for a variety of reasons. For example, the methods for incorporating synthetic polynucleotides into nucleic acids as described herein can be performed in conjunction with any library preparation method regardless of assay instrument (e.g., library preparation protocols for use in sequencing instrumentation including, but not limited to, those of Illumina, Inc., Applied Biosystems®, Ion Torrent®, 454 Life Sciences, Complete Genomics, Pacific Biosciences, Oxford Nanopore Technology, etc.). Further, practicing the methods described herein upstream of library preparation protocols allows the synthetic polymorphisms to be fixed and determinable prior to library preparation. Additionally, practicing the methods described herein provides for an initial fragmentation of genomic DNA into longer fragments, for example more than 100 bp, more than 300 bp, more than 500 bp, more than 1000 bp, more than 2000 bp, more than 10,000 bp, etc. Longer fragments, while typically not advantageous for next-generation sequencing, allow for the incorporation of more synthetic polymorphisms than would shorter fragments (e.g., <300 bp); as such providing a pattern of synthetic polymorphisms which, upon additional fragmentation of longer fragments into shorter fragments, can be readily discernible and alignable after sequencing. Another advantage of longer fragments is that longer fragments have the possibility of containing greater than one natural SNP as such more SNPs can be identified and aligned using fewer fragments.

In some embodiments, synthetic nucleotides can be incorporated into nucleic acids prior to nucleic acid fragmentation. For example, modified nucleotides could be incorporated into cellular nucleic acids during cell culture. Modified nucleotides could be incorporated into cellular nucleic acids for example by modifying the culture media to include the modified nucleotides in a concentration sufficient to cause incorporation of the modified nucleotides into cellular DNA.

In other embodiments, genomic DNA can be rendered into smaller genomic molecules comprising modified nucleotides without the need for mechanical, chemical, or biological fragmentation following by modified nucleotide incorporation. For example, instead of initial fragmenting of the genomic DNA by, for example mechanical or biological methods (e.g. transposon related methods), randomers (e.g., random sequence hexamers) could be utilized for creating a plurality of nucleic acid molecules derived from the genomic DNA template. For example, randomers could be hybridized to genomic DNA and extended (e.g., by rolling circle amplification) thereby creating long strands of DNA which would serve the same purpose of other forms of fragmentation disclosed herein (e.g., create smaller polynucleotides for library preparation for sequencing). The extension products resulting from the extension could then be used in bisulfite conversion methods for converting natural nucleotides to synthetic polymorphisms. In other embodiments, modified nucleotides (e.g., pPTP, 8-oxo-G, isoC, isoG, etc.) could be incorporated during the extension reaction resulting in extension products that contain the modified nucleotides thereby concatenating the steps of creating shorter molecules from genomic DNA comprising modified nucleotides, which can then be used for further library preparatory methods.

Regardless of method for incorporating synthetic polymorphisms into nucleic acid molecules, the resulting polynucleotides comprising the synthetic polymorphisms can be used for downstream assays. For example, the modified nucleic acid molecules can be utilized for sequencing. The nucleic acid molecules comprising the synthetic polymorphisms find particular utility for determining or characterizing a haplotype of a sample. The nucleic acid molecules comprising the synthetic polymorphisms also find particular utility for de novo sequencing where shorter sequence reads can be aligned and assembled to create full length, and sometimes novel, sequences. The nucleic acid molecules comprising the synthetic polymorphisms also find particular utility when sequencing regions in the genome that comprise high incidence of repeated regions which can be difficult to align due to their repetitive nature.

The random nature of incorporating the synthetic polymorphisms using the methods disclosed herein provides a modified nucleic acid molecule with a pattern of incorporated polymorphisms, that random pattern of which, once determined, can be aligned and reported for determining a sample haplotype (e.g. haplotype content or phase), a de novo sequence, verification of a sample sequence, the sequence of genomic locations that were previously deemed difficult to determine, etc. Sequences determined by practicing methods disclosed herein, for example a determined haplotype, can be used by diagnosticians, clinicians, researchers and other parties for example for correlating sequences to disease states (e.g., cancers, neurological disorders, degenerative disorders, etc.) information which in turn can be utilized to diagnose and predict whether or not an individual may or may not have, or may or may not have a predisposition to, a particular disease or disorder. Further, certain sequences, for example a haplotype, may be correlated to preferential treatment regimens for a particular disease or disorder which may be used by health care professionals to determine a treatment regimen specific to any particular individual. Additionally, methods can be used to determine the type and number of repeated regions in a genome, for example for forensic purposes.

In some embodiments, the modified nucleic acid molecules comprising synthetic polymorphisms can find particular utility in sequencing, for example for determining a haplotype, for de novo sequencing, etc. The modified nucleic acid molecules comprising synthetic polymorphisms can be sequenced by any means. Target nucleic acids, for example genomic DNA, are typically extracted and isolated from a sample prior to sequencing. Alternatively, RNA may be harvested from a sample and cDNA created from the isolated RNA, wherein the cDNA can be used for sequencing. The terms "nucleic acid" and "polynucleotide" refer to deoxyribonucleic acid (DNA), ribonucleic acid (RNA), complementary DNA (cDNA) or analogues of DNA, cDNA or RNA. The nucleic acids can be single stranded or double stranded molecules. The nucleic acids or polynucleotides may have originated in single stranded form, such as ssDNA or RNA, or they may have originated in double stranded form (dsDNA) such as that found in genomic DNA, amplification products, and/or fragments thereof, and the like. The nucleic acids or polynucleotides, regardless of stranded nature, may derive from any number of sources including, but not limited to, a sample from an entire genomic complement of an organism, a fragment of an entire genomic complement of an organism. Nucleic acids may include intronic and exonic sequences or any number of regulatory and/or non-regulatory sequences.

A sample can be from any source, for example, prokaryote, archaea or eukaryote. Further, a sample can be liquid (i.e., blood, serum, plasma, cerebral spinal fluid, urine, etc.) or solid (i.e., cells, tissues, etc.). As used herein, the term "sample" is used consistent with its meaning in the art of biology and chemistry. In one sense, it is meant to include a nucleic acid or polynucleotide or fragment thereof from a specimen or culture obtained from any source such as biological and environmental samples. Biological samples may be obtained from animals including, but not limited to humans, non-human primates, and non-human animals including, but not limited to, vertebrates such as rodents, ovines, bovines, ruminants, lagomorphs, porcines, caprines, equines, canines, felines, ayes, etc. Biological samples include, but are not limited to, fluids such as blood products, tissues, cells, and the like. Biological samples can further be of plant origin, monocotyledonous or dicotyledonous, deciduous or evergreen, herbaceous or woody, including but not limited to agricultural plants, landscape plants, nursery plants, and the like. Environmental samples may be bacterial, viral, fungal, and the like, in origin. Preferred samples are eukaryotic in origin. Particularly useful samples are those derived from organisms having more than one set of haploid chromosomes (the set being one or more different chromosomes). For example, a sample can be derived from an organism that is diploid, triploid or polyploid. Basically, any organismal nucleic acid sample source of interest to an investigator in determining sequence information is amenable to the present methods. A sample can also include a synthetic nucleic acid or fragment thereof. Derivatives or products of nucleic acids such as amplified copies or chemically modified species are also included. In preferred embodiments, a sample is derived from a mammal, for example a human.

A variety of methods and protocols are available for isolating nucleic acids (such as genomic DNA or RNA) from a sample as known to a skilled artisan, for example as described in Molecular Cloning: A Laboratory Manual (Eds., Sambrook, Fritsch and Maniatus, Cold Spring Harbor Laboratory), Current Protocols in Molecular Biology, John Wiley & Sons, Inc. (The Red Book) and Short Protocols in Molecular Biology, Eds., Ausubel et al., John Wiley & Sons, Inc. There are also a myriad of commercially available products and kits available for isolating DNA and RNA from a variety of sample types. The present disclosure is not intended to be limited by the way in which nucleic acids are isolated from a sample.

Following nucleic acid extraction and isolation from a sample, the nucleic acids can be processed further prior to sequencing, for example following library preparation protocols. Processing may differ depending on which sequencing instrument and technology is being utilized by the investigator. Methods and systems disclosed herein are not necessarily limited to any particular library preparation method or technology. FIGS. 1-3 exemplify practicing the disclosed methods, for example in some embodiments, prior to practicing library preparation. Even though there are advantages for performing the methods disclosed herein prior to typical library protocols wherein smaller fragments of genomic DNA are desired, the methods can be incorporated into the workflow of a typical library preparation methodology. For example, the methods disclosed herein could also be incorporated into any library preparation step prior to sequencing of the sample. As such, in some embodiments, the methods for incorporating synthetic polymorphisms into target DNA can be incorporated into a library workflow following library fragmentation of the sample and prior to sequencing the sample DNA. As an example, the method described herein may be incorporated into, or used in combination with, the sample preparation workflow for PACBIO RS DNA Template Preparation Kit (Pacific Biosciences, Inc., Menlo Park, Calif.) which utilizes SMRTbell™ technology library format where insert lengths for sequencing can be between 250 and 6000 bp long. An investigator can utilize PCR related methods for library preparation or can alternatively employ non-PCR based methods for library preparation.

As exemplified in FIGS. 1-3, in some embodiments genomic DNA represented as a pair of homologous chromosomes can be randomly fragmented into long pieces of DNA fragments, for example fragments at least 300 bp, at least 500 bp, at least 750 bp, at least 1000 bp, at least 2000 bp, at least 3000 bp, at least 5000 bp long. Random fragmentation can be accomplished by a variety of means known to a skilled artisan. For example, in some embodiments mechanical and/or acoustic shearing can be used to fragment genomic DNA such as by repeatedly forcing a genomic DNA sample through a small bore syringe, by nebulization, by hydroshearing or by sonication.

Initial fragmentation of nucleic acids can be the same or different as those utilized for a variety of library preparation protocols. Examples of nebulization effected fragmentation of DNA is described in the Paired-End Sample preparation kits by Illumina, Inc and in kits for generating library DNA utilized by the GS Junior and GS FLX sequencing systems of 454 Life Sciences (Branford, Conn.). In some embodiments, shearing of DNA is accomplished by hydrodynamic forces, for example as those provided by the DIGILAB® HydroShear technology instruments are described in the workflow for the SOLiD™ Mate Paired library kits (Applied Biosystems® Life Technologies, Carlsbad, Calif.). In some embodiments, shearing of DNA is accomplished by acoustic/mechanical means such as that provided by Covaris® adaptive focused acoustics (AFA) processes. In some embodiments, sonication may also be used for fragmenting genomic DNA for example as exemplified in the workflow of the SOLiD™ Fragment Library construction kits (Applied Biosystems® Life Technologies, Carlsbad, Calif.) wherein Covaris® sonication technology is utilized to shear genomic DNA. In some embodiments, transposon based technology can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA ("tagmentation") thereby creating a population of fragmented nucleic acid molecules which comprise unique adapter sequences at the ends of the fragments. Transposon based methodologies are particularly advantageous when long nucleic acid fragments are desired. In some embodiments, enzymatic fragmentation can be utilized to fragment genomic DNA, for example as employed in the workflow of Ion Plus and Ion Xpress™ Plus and fragment library kits (Ion Torrent™ Life Technologies, Carlsbad, Calif.). As demonstrated, there are a myriad methods for fragmenting large nucleic acid molecules, such as genomic DNA, and a skilled artisan will understand that the method may be determined based on a particular assay technology and instrument.

In some embodiments, once the nucleic acids for assay are initially fragmented into long fragments as previously described further processing of the sample may be performed. As exemplified in FIGS. 1-3, some embodiments comprise the affixation of additional sequences, such as adapter sequences, on the ends of nucleic acid fragments. Adapter sequences may be used for additional downstream methods such as amplification, polymerase chain reaction, molecule capture methods, and the like. Such adapter sequences may be primer sequences which may be the same or different than adapter sequences utilized in downstream library preparation kits and methods. Adaptors may be double stranded, single stranded, forked (i.e., a portion of the adaptor being double stranded and a portion of the adaptor being two single strands) or in hairpin configuration (i.e., a portion of the adaptor being double stranded and a portion being a single stranded loop structure). Adaptors could also include unique sequences, such as barcodes, useful in identifying a particular target DNA. The methods disclosed herein are not necessarily limited to any particular use or sequence of adapters, and a skilled artisan will understand that use of adapters may be chosen based on the assay and instrument being used.

FIGS. 1-3 show exemplary embodiments for incorporation of synthetic polymorphisms into nucleic acids. For example, as seen in FIGS. 1-3 the incorporation of a modified nucleotide (e.g., 8-oxo G), bisulfite conversion of C to U, and incorporation of a modified nucleotide (e.g., iC), respectively, can be performed for creating synthetic polymorphisms in nucleic acids. In some embodiments, the modified nucleotide 8-oxo G can be incorporated into double stranded DNA by exposing the nucleic acid fragments to oxygen free radical species and/or ionizing radiation. Alternatively, 8-oxo G can be incorporated into a nucleic acid by annealing and extension of a primer on the nucleic acid in the presence of canonical nucleotides dATP, dTTP, dCTP and a ratio of dGTP to the analog 8OxodGTP. In some embodiments, the ratio of dGTP to 8OxodGTP is at least 1:1, 1:2, 1:3, 1:4, 1:5, 1:10, 1:20, 1:30, 1:40, 1:50, 1:75, 1:99. In other embodiments the percentage of 8OxodGTP in a method for incorporating synthetic polymorphisms is 100% (i.e., no dGTP is added to a reaction). The same or similar process can be followed for incorporation of modified nucleotides such as iC and iG, as exemplified in FIG. 3. For partial bisulfite conversion, conventional methods for bisulfite conversion known to a skilled artisan can be followed for partial conversion of cytosines to uracils in DNA as exemplified in FIG. 2.

In some embodiments, one or more primers utilized to bind to the adapter sequences for incorporation of modified nucleotides by annealing and extension of the primers may be further associated with a binding moiety for effecting capture and purification of the modified nucleic acid strand from the non-modified strands (i.e., nucleic acid strands with no incorporated synthetic polymorphisms). As exemplified in FIGS. 1 and 3, the hapten biotin can be associated with a primer for subsequent capture by its binding partner streptavidin, thereby purifying it away from the non-modified nucleic acids. However, the present methods are not necessarily limited by a particular type or set of binding partners or capture system. In some embodiments, once the strand containing the modified nucleotide is captured and purified away from the non-modified strand, the modified strand can be duplicated and synthetic polymorphisms replicated, for example by primer binding to an adapter affixed to the end of a nucleic acid followed by duplication to create a double stranded nucleic acid molecule with incorporated synthetic polymorphisms.

In some embodiments, there is no selective capture of strands. For example, FIG. 2 demonstrates a method for incorporating synthetic polymorphisms wherein selective capture is not performed. This demonstrates that even though strand selection is advantageous it is not always required. In some embodiments, once a nucleic acid strand comprising modified nucleotides is purified and/or selected from its complement which does not comprise modified nucleotides the selected strand can be replicated by, for example, primer extension methods, wherein such replication or duplication incorporates synthetic polymorphisms opposite the location in the parent strand wherein resides the modified nucleotides. As exemplified in FIG. 1, duplication of the template nucleic acid strand comprising 8-oxo G results in a complementary strand comprising newly incorporated adenines (A) or occasionally cytosines (C) opposite the location of 8-oxo G nucleotides in the template strand. However, adenines are exemplary of a nucleotide which mispairs with 8-oxo G. Cytosines can also pair with the modified nucleotide 8-oxo G. As such, in some embodiments wherein 8-oxo G is utilized as the modified nucleotide for incorporating synthetic polymorphisms, adenines and/or cytosines can be incorporated as synthetic polymorphisms. When other modified nucleotides are utilized, the resulting synthetic polymorphism being incorporated can be a nucleotide which pairs with that specific modified nucleotide.

FIG. 1 demonstrates the removal of the exemplary modified nucleotide 8-oxo G prior to sequencing. The nucleotide 8-oxo G can pair with either adenines or cytosines, as such the maintenance of the 8-oxo G in a fragment for sequencing would not be preferential. In some embodiments, a modified nucleotide is maintained in nucleic acid fragments used for sequencing. For example, the incorporation of isoC (FIG. 3) into a nucleic acid fragment wherein, upon duplication, the nucleotide partner isoG is also incorporated thereby providing a nucleic acid for sequence comprising both isoC and isoG as synthetic polymorphisms.

In embodiments of the present application, the nucleic acid fragments comprising the synthetic polymorphisms can be amplified. Such amplification can enrich a library for only those nucleic acid fragments that comprise adapters at both ends as well as to increase the amount of DNA in the fragment pool going into the library preparation process. For example, polymerase chain reaction (PCR) amplification can be performed after incorporation of synthetic polymorphisms into nucleic acid fragments using primers that anneal to the adapters ligated to the ends of the nucleic acid fragments. Adapters as used herein may serve many functions, one of which is for hybridization to homologous sequences affixed to substrates, for example for performing emulsion PCR (emPCR) or clonal generation for use in sequence by synthesis methodologies.

After the target nucleic acids have been modified to comprise a plurality of synthetic polymorphisms, a library preparation for sequencing can be produced, for example, by performing the methods recommended by a particular sequencing method and instrument. For example, as described in protocols and manuals for use in any number of sequencing systems including, but not limited to, Illumina, Inc. (e.g., HiSeq 1000, HiSeq 2000, HiSeq 2500, MiSeq, Genome Analyzer systems, etc.), 454 Life Sciences (e.g., GS Junior, GS FLX+, etc.), Applied Biosystems® Life Technologies (e.g., SOLiD™ sequencing systems) and Ion Torrent™ Life Technologies (e.g., Ion PGM™ Sequencer, Ion Proton™ Sequencer, etc.). A DNA library sample may be further amplified for sequencing by, for example, multiple strand displacement amplification (MDA) techniques. A skilled artisan will recognize additional methods and technologies for producing nucleic acid libraries which could also be used in combination with methods described herein for incorporating synthetic polymorphisms into nucleic acid fragments. As such, embodiments described herein are not necessarily limited to any particular method for creating libraries, other than, in particular embodiments, the incorporation or creation of synthetic polymorphisms prior to or within those methods.

Nucleic acid libraries comprising synthetic polymorphisms are advantageous for use in sequencing assays, for example for determining haplotypes, de novo sequence determinations and forensic nucleotide applications (i.e., nucleotide repeat regions, etc.) to name a few. In some embodiments, DNA libraries comprising synthetic polymorphisms can be immobilized on a flowcell. The immobilized nucleic acids can be sequenced using single molecule resolution techniques or the immobilized nucleic acids can be amplified, for example via bridge amplification, for ensemble-based detection. Bridge amplification can be performed on the immobilized polynucleotides prior to sequencing, for example for sequence by synthesis methodologies. In bridge amplification, an immobilized polynucleotide (e.g., from a DNA library) is hybridized to an immobilized oligonucleotide primer. The 3' end of the immobilized polynucleotide molecule provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension. Thus, the first and second portions can be amplified to produce a plurality of clusters in a process known as "clustering". Clusters and colonies are used interchangeably and refer to a plurality of copies of a nucleic acid sequence and/or complements thereof attached to a surface. Typically, the cluster comprises a plurality of copies of a nucleic acid sequence and/or complements thereof, attached via their 5' termini to the surface. Exemplary bridge amplification and clustering methodology are described, for example, in PCT Patent Publ. Nos. WO00/18957 and WO98/44151, U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2005/0100900, U.S. Patent Publ. No. 2004/0002090; U.S. Patent Publ. No. 2007/0128624; and U.S. Patent Publ. No. 2008/0009420, each of which is incorporated herein by reference in its entirety. The compositions and methods as described herein are particularly useful in sequence by synthesis methodologies utilizing a flowcell comprising clusters.

Emulsion PCR (emPCR) methods for amplifying nucleic acids prior to sequencing can also be used in combination with methods and compositions as described herein. Emulsion PCR comprises PCR amplification of an adaptor flanked shotgun DNA library in a water-in-oil emulsion. The PCR is multi-template PCR; in particular embodiments only a single primer pair is used. One of the PCR primers is tethered to the surface (5' attached) of microscale beads. A low template concentration results in most bead-containing emulsion microvesicles having zero or one template molecule present. In productive emulsion microvesicles (an emulsion microvesicle where both a bead and template molecule are present), PCR amplicons can be captured to the surface of the bead. After breaking the emulsion, beads bearing amplification products can be selectively enriched. Each clonally amplified bead will bear on its surface PCR products corresponding to amplification of a single molecule from the template library. The beads can then be arrayed on a surface of a flow cell for sequencing. Various embodiments of emulsion PCR methods are set forth in Dressman et al., Proc. Natl. Acad. Sci. USA 100:8817-8822 (2003), PCT Patent Publ. No. WO 05/010145, U.S. Patent Publ. Nos. 2005/0130173, 2005/0064460, and 2005/0042648, each of which is incorporated herein by reference in its entirety.

DNA nanoballs can also be used in combination with methods and compositions as described herein. Methods for creating and utilizing DNA nanoballs for genomic sequencing can be found at, for example, U.S. Pat. Nos. and publications U.S. Pat. No. 7,910,354, 2009/0264299, 2009/0011943, 2009/0005252, 2009/0155781, 2009/0118488 and as described in, for example, Drmanac et al., 2010, Science 327(5961): 78-81; all of which are incorporated herein by reference in their entireties. Briefly, following genomic library DNA fragmentation adaptors are ligated to the fragments, the adapter ligated fragments are circularized by ligation with a circle ligase and rolling circle amplification is carried out (as described in Lizardi et al., 1998. Nat. Genet. 19:225-232 and US 2007/0099208 A1, each of which is incorporated herein by reference in its entirety). The extended concatameric structure of the amplicons promotes coiling thereby creating compact DNA nanoballs. The DNA nanoballs can be captured on substrates, preferably to create an ordered or patterned array such that distance between each nanoball is maintained thereby allowing sequencing of the separate DNA nanoballs. In some embodiments such as those used by Complete Genomics (Mountain View, Calif.), consecutive rounds of adapter ligation, amplification and digestion are carried out prior to circularization to produce head to tail constructs having several genomic DNA fragments separated by adapter sequences.

Disclosed methods for determining a haplotype, de novo sequence, etc. by incorporation of synthetic polymorphisms into a polynucleotide or fragment thereof find particular utility when used in sequencing, for example next generation ("nexgen") sequencing by synthesis (SBS) technologies. Sequencing by synthesis generally comprises sequential addition of one or more nucleotides to a growing polynucleotide chain in the 5' to 3' direction using a polymerase. The extended polynucleotide chain is complementary to the nucleic acid template affixed on the substrate (e.g., flowcell, chip, slide, etc.); the target sequence comprising the synthetic polymorphism.

Disclosed method for determining haplotype, de novo sequence, etc. by incorporation of synthetic polymorphisms into a polynucleotide or fragment thereof also find utility when used in sequencing by ligation, sequencing by hybridization, and other sequencing technologies. An exemplary sequence by ligation methodology is di-base encoding (e.g., color space sequencing) utilized by Applied Biosystems' SOLiD™ sequencing system (Voelkerding et al., 2009, Clin Chem 55:641-658; incorporated herein by reference in its entirety). Sequence by hybridization comprises the use of an array of short sequences of nucleotide probes to which is added fragmented, labeled target DNA (Drmanac et al., 2002, Adv Biochem Eng Biotechnol 77:75-101; Lizardi et al., 2008, Nat Biotech 26:649-650, U.S. Pat. No. 7,071,324; incorporated herein by reference in their entireties). Further improvements to sequence by hybridization can be found at, for example, US patent application publications 2007/0178516, 2010/0063264 and 2006/0287833 (incorporated herein by reference in their entireties). Sequencing approaches which combine hybridization and ligation biochemistries have been developed and commercialized, such as the genomic sequencing technology practiced by Complete Genomics, Mountain View, Calif. For example, combinatorial probe-anchor ligation, or cPAL™ (Drmanac et al., 2010, Science 327(5961): 78-81) utilizes ligation biochemistry while exploiting advantages of sequence by hybridization. The methods for haplotyping, de novo sequencing, etc. disclosed herein could be utilized in combinatorial probe-anchor ligation sequencing technologies. It is contemplated that the methods as described herein for use of synthetic polymorphisms to determine haplotype, de novo sequence, etc. are not limited by any particular sequencing methodology. Additional sequencing technologies include, but are not limited to, those practiced by one or more of polony sequencing technology (Dover Systems), sequencing by hybridization fluorescent platforms (Complete Genomics) and sTOP technology (Industrial Technology Research Institute).

Single molecule sequencing can also be used with methods as disclosed herein. For example, non-amplified DNA libraries for sequencing can be prepared as previously described. The library fragments can be hybridized and captured on a substrate such as a flow cell and assayed on, for example, a HeliScope™ Single Molecule Sequence instrument. Further description of single molecule sequencing can be found at, for example, Puchkarev et al. (2009, Nat. Biotechnol. 27:847-52, incorporated herein by reference in its entirety) and Thompson and Steinmann (2010, Curr. Prot. Mol. Biol. Cpt 7, Unit 7.10, incorporated herein by reference in its entirety).

The methods set forth herein can be used in combination with nucleic acid detection systems such as those provided by Illumina®, Inc. (HiSeq 1000, HiSeq 2000, HiSeq 2500, Genome Analyzers, MiSeq, HiScan, iScan, BeadExpress systems), Applied Biosystems™ Life Technologies (ABI PRISM® Sequence detection systems, SOLiD™ System), Ion Torrent™ Life Technologies (Ion PGM™, Ion Proton™) 454 Life Sciences (GS Junior, GS FLX+), PacBio RS (Pacific Biosciences®), Oxford Nanopore Technologies® (GridION, MinION) or other sequencing instruments, further as those described in, for example, U.S. Pat. Nos. and patent applications U.S. Pat. Nos. 5,888,737, 6,175,002, 5,695,934, 6,140,489, 5,863,722, 2007/007991, 2009/0247414, 2010/0111768 and PCT application WO2007/123744, and U.S. patent application Ser. Nos. 61/431,425, 61/431,440, 61/431,439, 61/431,429, 61/438,486 each of which is incorporated herein by reference in its entirety.

Output from a sequencing instrument can be of any sort. For example, some current technologies utilize a light generating readable output, such as fluorescence or luminescence. Other technologies utilize semiconductors which detect ion release and digitally output sequence based on hydrogen ions released during incorporation of nucleotides during sequencing. However, the present methods are not limited to the type of readable output as long as differences in output signal for a particular sequence of interest is potentially determinable.

Examples of analysis software that may be used, or modified, to characterize output derived from practicing methods as described herein include, but are not limited to, Pipeline, CASAVA and GenomeStudio data analysis software (Illumina®, Inc.), SOLiD™, DNASTAR® SeqMan® NGen® and Partek® Genomics Suite™ data analysis software (Life Technologies), Feature Extraction and Agilent Genomics Workbench data analysis software (Agilent Technologies), Genotyping Console™, Chromosome Analysis Suite data analysis software (Affymetrix®). It is contemplated that one or more software programs for use with methods and compositions disclosed herein will have the capacity to recognize the incorporated synthetic polymorphism patterns present in the fragment sequence data, align the polymorphisms identified in the fragment sequence data and output a sequence based on that alignment. In some embodiments, the output may comprise a haplotype (e.g. haplotype content or phase) for the target sample. In other embodiments, the output may comprise de novo sequence information for the target sample. In other embodiments, output may comprise forensic nucleotide repeat information, such a type (i.e., sequence of repeat, location of repeat, number of short or intermediate tandem repeats, etc.

In some embodiments, sequence analysis and alignment comprises aligning the sequence reads against a reference genome, or de novo assembly of alignable regions, for example by barcoding introduced into the library fragments for sequencing as known to a skilled artisan. Depending on the density of the artificial SNPs, it is contemplated that standard alignment software tools could be used. For example, if synthetic SNP density is high, then alignment programs could be modified such that alignments are adequately permissive enough to place sequence reads. As an example, existing modified alignment pipelines for bisulfite sequencing could be used when synthetic SNPs are incorporated by bisulfite conversion methodologies (e.g., as described at www.bioinformatics.babraham.ac.uk/projects/bismark). For de novo assembly, it is contemplated that built-in error correction modules can be disabled for standard short read assemblers when reading sequence derived from practicing methods disclosed herein (2008, Zerbino and Birney, 2008, Genome Res 18:821-829, incorporated herein by reference in its entirety).

Algorithms for building haplotype blocks from short-sequence reads could be used with methods disclosed herein (Bansal and Bafna, 2008, Bioinformatics 24:i153-i159). Such algorithms may, however, be modified away from the standard assumption of two discrete haplotypes as would be expected when sequencing a normal diploid human DNA molecule. For example, the introduced synthetic SNPs would result in a larger number of apparent or artificial haplotypes corresponding to each original sequence fragment and therefore modifications would be made in the algorithms to accommodate this non-standard information.

The synthetic SNPs could be identified from normal nucleotide sequences in a number of ways. For example, the original sequence which has not been modified could serve as the reference sequence and therefore as the control without the synthetic SNPs. In this method, the polymorphisms that are not present in the original sequence could be identified and correlated with those locations in the modified sequence, thereby identifying the locations in the modified sequence where synthetic SNPs were incorporated. Alignment could then take place using those identified modified nucleotides. For consensus calling, the synthetic polymorphisms would be expected to be unique to the original sequence. As such, by sequencing original fragments at a particular genomic position, the frequency of the polymorphisms across the synthetic haplotypes could be estimated and compared to the expected frequency in a normal diploid human sample.

In some embodiments, the merging of artificial haplotypes can be performed by algorithms which are modified to identify the synthetic polymorphisms, such as HapCUT or modifications thereto (2009, Bansal and Bafna). The algorithms could be modified to merge SNPs identified as non-synthetic SNPs but derived from different synthetic haplotypes, thereby creating the true underlying haplotype aligned map.

In some embodiments, output from aligned sequences comprising both natural and synthetic polymorphisms could include both the locations of the natural polymorphisms and the locations of the synthetic polymorphisms in the reconstructed haplotype. Alternatively, output could include just the natural polymorphisms in the reconstructed haplotypes with the synthetic polymorphisms being screened out. Visualization can be accomplished in a number of ways, for example a standard genome browser such as an integrative genomics viewer (IGV) could be utilized (2011, Robinson et al., Nat Biotech 29:24-26, incorporated herein by reference in its entirety). The reconstructed haplotypes could be annotated in the genome browser to highlight the positions of the true, natural polymorphisms and/or the synthetic polymorphisms (e.g., if present in the output). However, other visualization tools may also be used as known to a skilled artisan. The present methods are not necessarily limited to the algorithms, methods or systems used for aligning and outputting or visualizing the sequences derived from practicing the methods disclosed herein.

EXAMPLES

The following examples are provided in order to demonstrate and further illustrate certain preferred embodiments and aspects of the disclosed methods and compositions and are not to be construed as limiting the scope thereof.

Prior to library preparation the genomic DNA can be modified to include artificial polymorphisms. The genomic DNA can be initially fragmented into large pieces (for example several kilobases). The larger fragment size maximizes the occurrence of two or more artificial SNPs in the same fragment while maximizing the occurrence of more heterozygous SNPs. Transposon mediated fragmentation of nucleic acids and hydroshearing are examples of methods for generating initial DNA fragments of, for example, between 1,000-40,000 bp.

Example 1—Synthetic Polymorphism Incorporation into phiX Genome

Sequencing experiments were performed to assess the frequency of incorporation of modified nucleotides into a DNA strand for downstream sequencing. A bacteriophage reference genome, phi X 174 or phiX was used as phiX has a small, well defined genomic sequence of 5386 bases. The two modified nucleosides, 8OxodGTP and dPTP, were incorporated in different combinations with normal dNTPs. dPTP can base-pair to both A and G whereas 8OxoG can base pair to both A and C.

A standard paired end Illumina flow cell was seeded with a standard phiX library at a concentration of 2 pM following manufacturer's protocols. Following hybridization of the library to the flowcell bound oligonucleotides, DNA molecules were copied in the flowcell lanes using the first strand extension method by incubating the flow cell at 40° C. for 1 hour in the presence of a DNA polymerase and various nucleotide mixes (natural and unnatural) as found in Table 1.

TABLE 1 phiX first extension assay with deoxynucleoside concentrations

| Lane 1 | [dATP] | [dCTP] | [dGTP] | [dTTP] | [8oxo-dGTP] | [dPTP] |
|---|---|---|---|---|---|---|
| 1 | 100 μM | 100 μM | 100 μM | 100 μM | | |
| 2 | 100 μM | 100 μM | | 10 μM | 100 μM | |
| 3 | 100 μM | | 100 μM | | | 100 μM |
| 4 | 100 μM | 10 μM | 100 μM | 10 μM | | 90 μM |
| 5 | 100 μM | | | | 100 μM | 100 μM |
| 6* | 100 μM | 10 μM | 10 μM | 10 μM | 90 μM | 90 μM |
| 7 | 100 μM | | 100 μM | | | 100 μM |
| 8 | 100 μM | 10 μM | 100 μM | 10 μM | | 90 μM |

*μM concentrations were rounded up to the nearest whole number

Following the first extension reaction (exemplified in FIG. 6), single molecules were clonally amplified by 35 cycles of isothermal amplification following manufacturer's protocols to yield amplification clusters which were sequenced on an Illumina Genome Analyzer. Reads were 100 cycles and data was analyzed using the standard system software followed by alignment to the phi X reference sequence using PhageAlign system software for paired end analysis.

Table 2 shows a summary of a sequencing run for each lane of the flowcell. Lane 1 is the control lane and is representative of sequencing output from a normal sequencing run using normal dNTPs. Lanes 2-6 show sequencing run output when one or both modified nucleotides are incorporated in combination with, or replacing, normal dNTPs during first strand extension (dNTP concentrations from Table 1). The % Error Rate (PF) reports the percentage of called bases in aligned reads that do not match up with the reference genome which, in this experiment, is reflective of the incorporation of the modified nucleotides into the target phiX DNA. As seen in Table 2, all the lanes where reaction conditions incorporated modified nucleotides into the phiX DNA showed a higher error rate than the normal control (Lane 1).

TABLE 2

Sequencing run for phiX modified DNA

| Lane Info | | Tile Mean +/- SD for Lane | | | |
|---|---|---|---|---|---|
| Lane | Lane Yield (kbases) | Clusters (raw) | Clusters (PF) | 1st Cycle Int (PF) | % intensity after 20 cycles (PF) |
| 1 | 92637 | 114410 +/- 5332 | 91720 +/- 36408 | 361 +/- 9 | 70.08 +/- 31.37 |
| 2 | 56566 | 83912 +/- 14512 | 56006 +/- 24144 | 338 +/- 17 | 67.14 +/- 32.57 |
| 3 | 45253 | 75960 +/- 13622 | 49783 +/- 10991 | 295 +/- 37 | 51.47 +/- 13.47 |
| 4 | 90758 | 122472 +/- 4426 | 99844 +/- 5727 | 290 +/- 29 | 73.47 +/- 15.73 |
| 5 | 6402 | 24030 +/- 7123 | 6338 +/- 4425 | 430 +/- 294 | 65.25 +/- 37.13 |
| 6 | 105230 | 133723 +/- 29330 | 104188 +/- 36207 | 284 +/- 68 | 93.66 +/- 51.01 |
| 7 | 56525 | 70834 +/- 17637 | 55965 +/- 14949 | 292 +/- 16 | 71.40 +/- 5.23 |
| 8 | 122200 | 142677 +/- 29937 | 120990 +/- 24005 | 344 +/- 37 | 85.12 +/- 2.47 |

| Lane Info | | Tile Mean +/- SD for Lane | | | |
|---|---|---|---|---|---|
| Lane | Lane Yield (kbases) | % PF Clusters | % Align (PF) | Alignment Score (PF) | % Error Rate (PF) |
| 1 | 92637 | 80.44 +/- 32.39 | 100.00 +/- 0.32 | 247727.68 +/- 728715.67 | 3.05 +/- 5.52 |
| 2 | 56566 | 70.95 +/- 33.52 | 100.00 +/- 0.32 | 10552.33 +/- 5267.76 | 4.45 +/- 2.98 |
| 3 | 45253 | 65.80 +/- 9.74 | 100.00 +/- 0.27 | 3894.09 +/- 1202.16 | 27.22 +/- 3.36 |
| 4 | 90758 | 81.55 +/- 4.15 | 100.00 +/- 0.15 | 8408.26 +/- 1141.61 | 7.78 +/- 2.19 |
| 5 | 6402 | 30.89 +/- 22.39 | 99.93 +/- 0.17 | 965602.29 +/- 1247823.10 | 26.79 +/- 2.94 |
| 6 | 105230 | 77.47 +/- 20.35 | 100.00 +/- 0.00 | 8615.87 +/- 627.55 | 7.17 +/- 0.18 |
| 7 | 56525 | 78.71 +/- 1.89 | 100.00 +/- 0.00 | 5619.21 +/- 388.95 | 24.94 +/- 0.13 |
| 8 | 122200 | 84.96 +/- 1.10 | 100.00 +/- 0.00 | 9267.62 +/- 149.03 | 6.71 +/- 0.14 |

FIG. 7 shows graphs of cycle versus error rates for the control (A) lane compared to Lanes 2 (B), 3 (C) and 4(D) (lane 6 results were basically the same as lane 4). As demonstrated in FIG. 7, the lanes wherein first strand extension incorporated modified nucleotides (Lanes 2, 3 and 4) show elevated error rates in comparison to the control Lane 1. Further the error rates do not increase but remain constant as such it appears that additional synthetic nucleotides are not incorporated after the first extension reaction, thereby removing the potential variable for accurate sequencing determination due to unexpected synthetic nucleotide incorporation during cluster formation and subsequent sequencing.

Sequencing data from phiX unmodified DNA showed that the majority of sequence reads had minimal or no sequencing errors, whereas those sequence reads derived from first strand extension reactions incorporating modified nucleotides had a high number of errors. FIG. 8 shows that incorporating the modified nucleotides into first strand extension resulted in a large number of sequenced fragments containing 1, 2, 3, 4 or more synthetic SNPs relative to the control, which would allow for fragment alignment of synthetic SNPs and hence haplotype determination. It was further determined which types and frequencies of synthetic SNPs resulted from the different combinations of natural and modified as found in Table 1.

Figure 9:
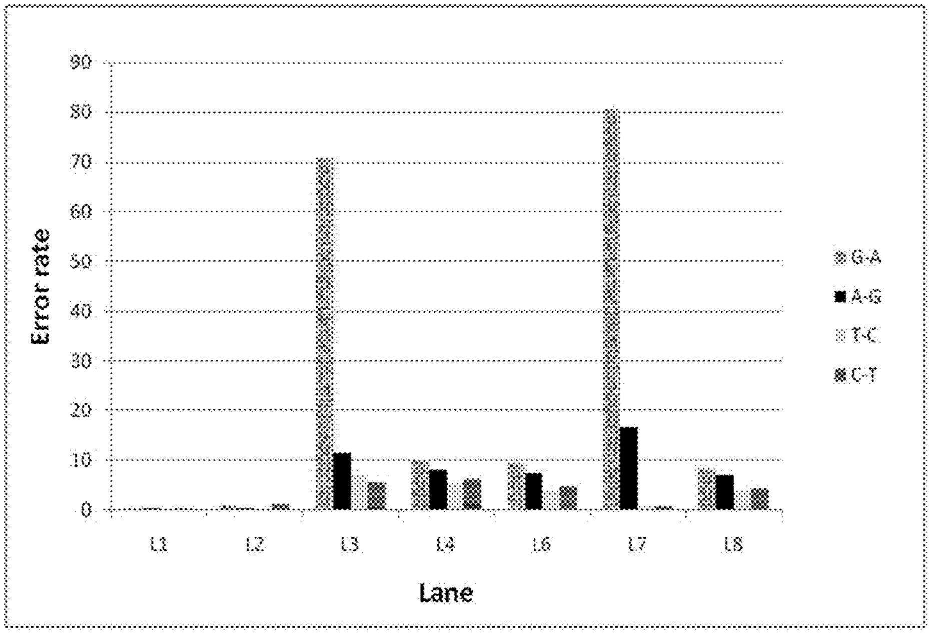
FIG. 9 shows a composite of the types and frequency (error rate) of synthetic polymorphisms that were introduced into the phiX template DNA for each flowcell lane during first strand extension.

FIG. 9 shows a lane by lane comparison of the mutations resulting from the use of dPTP during incorporation and prevalence (error rate) in the sequencing reads. As previously stated, dPTP can base-pair to both A and G thereby allowing for the following mutations to occur when dPTP is incorporated into the first strand extension product; A→G, G→A, T→C and C→T. When dPTP is incorporated in the absence of dCTP and dTTP (lanes 3 and 7 in FIG. 9) the G→A mutation dominates over other types of mutations. Conversely, when small amounts of dCTP and dTTP are present during the incorporation reaction (lanes 4, 6 and 8) that mutational domination is minimal.

Figure 10:
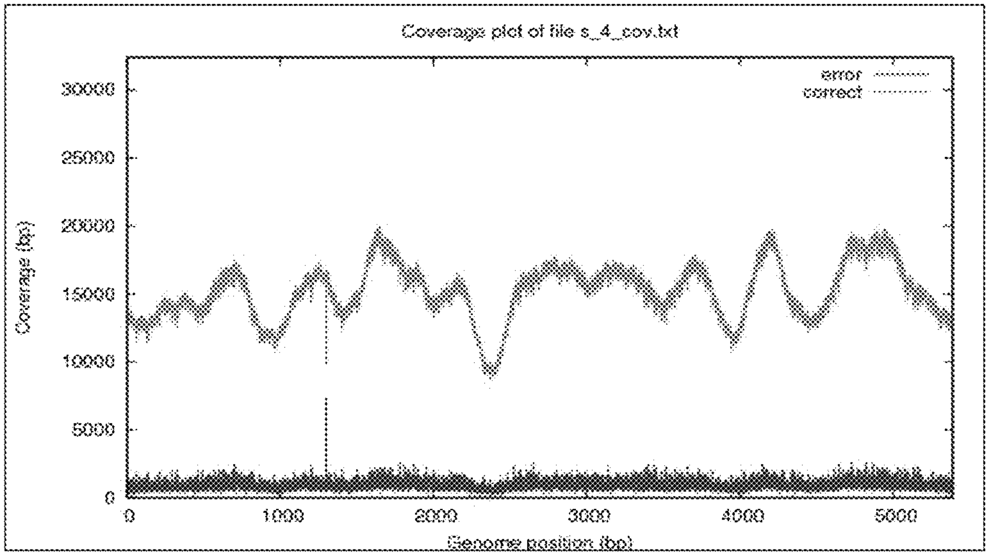
FIG. 10 A-C are representative of the distribution or coverage of artificial polymorphisms introduced into a phiX template DNA.

Additionally, the distribution pattern of the incorporated artificial SNPs was evaluated. As demonstrated in FIG. 10, incorporation of both 8OxoG (lane 2) and dPTP (lanes 3 and 4) was uniform over the entire genome. The spike in the figures is artifactual and does not represent a disproportionate amount of synthetic SNPs at this location.

It is contemplated that reaction conditions for Lane 5 were too extreme, resulting in sequencing failure for this lane.

Example 2—Synthetic Nucleotide Incorporation into p53 Gene

A region of the p53 gene was further sequenced using PTP modified nucleotide inserted into the gene prior to sequencing. A region of the p53 gene was amplified using oligonucleotides TP53 Exon1 3.1F (Tail-GAAACTTTCCACTTGATAAGAGGTC) and TP53 Exon 4 8.1R (Tail-GCCCCTGTCATCTTCTGTCC). The PCR mix consisted of 1× Thermopol buffer, 26 U/ml of Taq DNA polymerase, 0.52 μM of each oligonucleotide. Reaction 1 contained 200 μM of each natural nucleotide (dATP, dCTP, dGTP, dTTP). Reaction 2 contained approximately 200 uM of dATP and dGTP, 198 μM of dCTP and dTTP and 2 μM of dPTP. Reaction 3 contained approximately 200 μM of dATP and dGTP, 180 μM of dCTP and dTTP and 20 μM of dPTP. Amplification was carried out using the following conditions: 94° C. for 3 minutes followed by 38 cycles of 94° C. for 30 seconds, 50° C. for 30 seconds, 72° C. for 5 minutes. After cycling, samples were incubated at 72° C. for 5 minutes and the temperature was lowered to 4° C. The p53 target template was an aliquot of a PCR product amplified from sample NA18507 (human 1) using Phusion polymerase in a master mix (1× final concentration). A negative control (no template) was also included.

PCR reactions 1 and 3 were loaded onto a SYBR® Safe pre-stained 1% agarose gel in TAE and the gel bands of the expected size were excised using the QIAQuick Gel extraction kit following manufacturer's protocol. DNA was eluted in 30 μl of Elution Buffer. A second round of amplification was performed with Phusion polymerase in HiFi buffer with the primers previously described. One μl of the previous eluted DNA was used as template for the second PCR reaction (100 μl total volume). PCR conditions were as follows: 98° C. for 1 minute followed by 38 cycles of 98° C. for 10 seconds, 50° C. for 30 seconds, 72° C. for 5 minutes. After cycling, samples were incubated at 72° C. for 5 minutes and stored at 4° C. PCR reactions were loaded onto a SYBR® Safe pre-stained 1% agarose gel in TAE and the DNA bands of the expected size were excised using a QIAQuick Gel extraction kit. DNA was eluted in 30 μl of EB.

Eluted DNA was A-tailed at 74° C. for 30 minutes with dATP and Taq in 1× Thermopol buffer in a total volume of 10 μl per sample following standard protocols. A 3.5 μl aliquot of A-tailed DNA was ligated into pGEM®-T Easy vector (Promega) using Quick ligase (New England Biolabs). Ligations were transformed into XL10 Gold competent cells (Stratagene). After an overnight incubation at 37° C. on antibiotic containing agar plates, single colonies were picked and inoculated into Luria Broth. Plasmid DNA was prepared from approximately 3 ml of bacterial culture from each clone using a QIAprep Spin Miniprep kit (QIAGEN). Plasmid DNA was eluted in 50 μl of EB. Clones were screened for the presence of the insert by restriction enzyme digestion with EcoRI. Positive clones (three clones from the PCR with natural dNTPs and 6 clones from the PCR in the presence of dPTP) were sequenced by capillary sequencing with the SP6 and T7 primers homologous to pGEM®-T Easy vector sequences and also with an internal primer specific to the p53 sequence inserts for verification of modified nucleotide incorporation.

Figure 11:
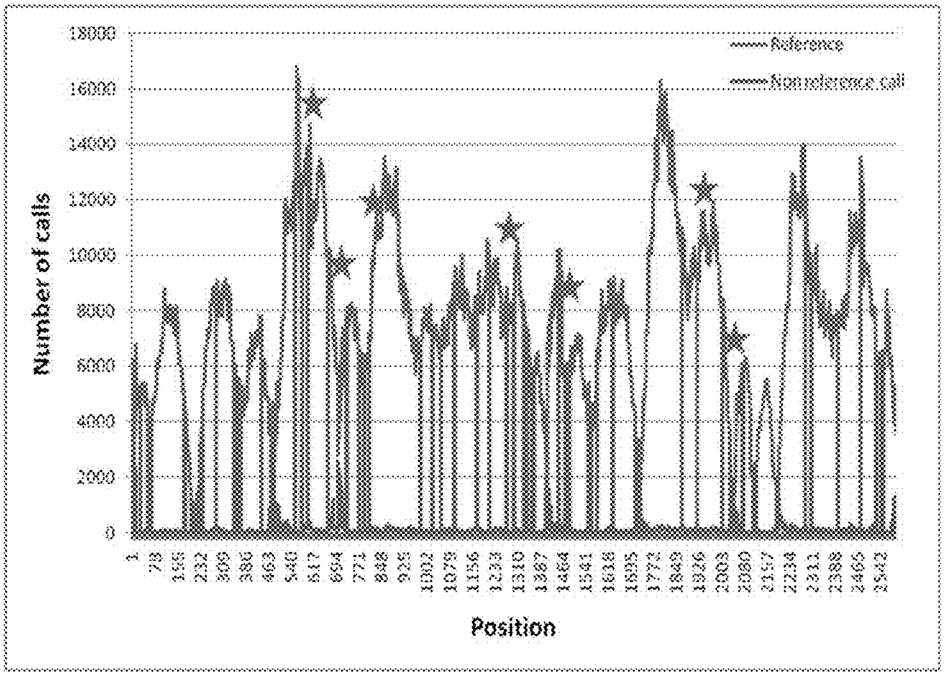
FIG. 11 shows coverage plots representing the sequencing data of three clones Panel A) Clone A, Panel B) Clone B and Panel C) Clone D. The graphs represent the coverage and locations of synthetic and natural heterozygous SNPs incorporated into p53 gene sequences derived from the DNA of a Yoruban male (NA18507). Each graph reports the sequence in the approximate same region of the p53 gene for each clone and the stars mark the approximate locations of natural heterozygous SNPs among the randomly distributed introduced synthetic SNPs. The top horizontal line with peaks represents the reference calls and the continuous baseline with vertical peaks under the horizontal line represents the non-reference calls.

FIG. 11 shows the SBS sequencing results from three random clones A, B and D. The sequences represent sequence runs from a region of a p53gene demonstrating natural SNPs interspersed with incorporated synthetic SNPs. The approximate locations of the natural heterozygous SNPs are represented by stars on the graphs. The vertical lines represent locations of SNPs and demonstrate the random and spatially distributed nature of the synthetic SNP incorporation.

Based on sequencing data, it was determined that naturally occurring SNPs were correctly identified and aligned in a sequenced section from the p53 gene with an average sequence read length of approximately 800 bp of determinable sequence.

All publications and patents mentioned in the present application are herein incorporated by reference. Various modifications and variations of the described methods and compositions of the present disclosure will be apparent to those skilled in the art without departing from the scope and spirit of the invention.

A number of embodiments have been described. Although the invention has been described in connection with specific preferred embodiments, it should be understood that the invention as claimed should not be unduly limited to such specific embodiments. Indeed, various modifications of the described methods as disclosed herein that are obvious to those skilled in the relevant fields are intended to be within the scope of the following claims.

What is claimed is:

1. A method for determining the sequence of a nucleic acid sample comprising:

a) providing a first plurality of nucleic acid fragments having a first length, wherein said plurality comprises parental chromosome fragments of maternally and paternally inherited chromosomes from a diploid, triploid or polyploid organism, wherein individual fragments in said first plurality comprise naturally occurring polymorphisms that form a haplotype and a plurality of synthetic polymorphisms, the plurality of synthetic polymorphisms forming different patterns on individual fragments of maternally inherited chromosomes relative to corresponding paternally inherited chromosomes and to other corresponding fragments of the maternally inherited chromosomes, such that individual fragments from an individual maternally inherited chromosome having an individual pattern of the different patterns are distinguishable from individual fragments of a corresponding individual paternally inherited chromosome and from the other corresponding fragments of the maternally inherited chromosomes that do not have the individual pattern and wherein the plurality of synthetic polymorphisms forming the different patterns are formed by modifying the nucleic acids by partial and incomplete bisulfate conversion of cytosines in the plurality of nucleic acid fragments;

b) preparing a nucleic acid library from said first plurality of nucleic acid fragments, wherein said nucleic acid library comprises a second plurality of nucleic acid fragments of a second length less than that of said first length, wherein naturally occurring polymorphisms of a haplotype are separated on different nucleic acid fragments of said second plurality, wherein each of said nucleic acid fragments of said second plurality has a first pattern of said plurality of synthetic polymorphisms that is the same as a second pattern of said plurality of synthetic polymorphisms present in another nucleic acid fragment of said second plurality of nucleic acid fragments, wherein the first pattern and the second pattern are from only one of the individual maternally inherited chromosome or the corresponding individual paternally inherited chromosome and the different patterns comprise the first pattern and the second pattern, c) sequencing nucleic acid fragments of said nucleic acid library, d) aligning the plurality of synthetic polymorphisms among the nucleic acid fragments that are sequenced using said first pattern and said second pattern to determine the sequence of the nucleic acid sample, wherein said sequence comprises said naturally occurring polymorphisms of said haplotype, and (e) determining that the sequence includes the naturally occurring polymorphisms of said haplotype on one of the individual maternally inherited chromosome or the corresponding individual paternally inherited chromosome.

2. The method of claim 1, wherein said aligning comprises matching additional patterns of synthetic polymorphisms of the plurality of nucleic acid fragment sequences thereby creating a sequence alignment based on the plurality of synthetic polymorphisms in the second plurality of nucleic acid fragments.

3. The method of claim 1, wherein said sequencing is a method selected from the group consisting of sequencing by synthesis, sequencing by hybridization, sequencing by ligation, single molecule sequencing, nanopore sequencing, and pyrosequencing.

4. The method of claim 1, wherein said sequencing comprises fluorescence detection.

5. The method of claim 2, wherein said matching is performed by a computer implemented method.

6. The method of claim 1, wherein said sequencing comprises sequencing by synthesis.

7. The method of claim 1, wherein said sequencing comprises sequencing by hybridization.

8. The method of claim 1, wherein said sequencing comprises sequencing by ligation.

9. The method of claim 1, wherein said sequencing comprises nanopore sequencing.

10. The method of claim 1, wherein said sequencing comprises pyrosequencing.

11. The method of claim 1, comprising determining that the naturally occurring polymorphisms of the haplotype are located on the individual maternally inherited chromosome or the corresponding individual paternally inherited chromosome.

12. The method of claim 1, comprising determining that a first of the naturally occurring polymorphisms of the haplotype is located on the individual maternally inherited chromosome and a second set of the naturally occurring polymorphisms of the haplotype is located on the corresponding individual paternally inherited chromosome.

13. The method of claim 1, wherein step a) comprises modifying a first plurality of nucleic acid fragments of a first length to incorporate modified nucleotides thereby providing the first plurality of nucleic acid fragments having the first length, wherein said plurality comprises parental chromosome fragments of maternally and paternally inherited chromosomes from the diploid, triploid or polyploid organism, wherein individual fragments in said first plurality comprise naturally occurring polymorphisms that form the haplotype and the plurality of synthetic polymorphisms, the plurality of synthetic polymorphisms forming different patterns on maternally inherited chromosomes relative to corresponding paternally inherited chromosomes, such that the individual maternally inherited chromosome is distinguishable from the corresponding individual paternally inherited chromosome based on the different patterns.

14. The method of claim 13, wherein the modifying comprises incorporating a mixture of unmodified nucleotides and the modified nucleotides into the first plurality of nucleic acid fragments during an extension reaction.

15. The method of claim 1, wherein said naturally occurring polymorphisms that form said haplotype are at a distance on the nucleic acids of said first plurality that is greater than said second length.

16. The method of claim 1, wherein said sequencing has a read length and wherein said naturally occurring polymorphisms that form said haplotype are at a distance on the nucleic acids of said first plurality that is greater than said read length.

17. The method of claim 1, further comprising a step of amplifying the first plurality of nucleic acid fragments prior to step b).

18. The method of claim 1, wherein the plurality of synthetic polymorphisms are present in greater frequency than the naturally occurring polymorphisms in the first plurality.

19. The method of claim 17, wherein the amplifying results in an enrichment of nucleic acid fragments of the second length within the nucleic acid library that include the first pattern or the second pattern.

20. A method for determining the sequence of a nucleic acid sample comprising:

a) providing a first plurality of nucleic acid fragments having a first length, wherein said plurality comprises parental chromosome fragments of maternally and paternally inherited chromosomes from a diploid, triploid or polyploid organism, wherein individual fragments in said first plurality comprise naturally occurring polymorphisms that form a haplotype and a plurality of synthetic polymorphisms introduced into the individual fragments of the first plurality such that different patterns of the synthetic polymorphisms are formed on the individual fragments of the first plurality of nucleic acid fragments relative to one another and such that individual fragments from an individual maternally inherited chromosome having an individual pattern of the different patterns are distinguishable from individual fragments of a corresponding individual paternally inherited chromosome and from the other corresponding fragments of the maternally inherited chromosomes that do not have the individual pattern;

b) preparing a nucleic acid library from the first plurality of nucleic acid fragments to generate a second plurality of nucleic acid fragments of a second length less than that of the first length such that the naturally occurring polymorphisms of the haplotype are separated on different nucleic acid fragments of the second plurality, and wherein the different nucleic acid fragments each comprise a same individual pattern of the different patterns on an overlapping portion of the different nucleic acid fragments, c) sequencing nucleic acid fragments of said nucleic acid library, d) aligning the overlapping portion comprising the same individual pattern among the different nucleic acid fragments that are sequenced to determine the sequence of the nucleic acid sample, wherein the sequence comprises the naturally occurring polymorphisms of the haplotype, and (e) determining that the sequence including the naturally occurring polymorphisms of the haplotype is from only one of an individual maternally inherited chromosome or a corresponding individual paternally inherited chromosome.

* * * * *

```
SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1

gaaactttcc acttgataag aggtc                                   25


<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2

gcccctgtca tcttctgtcc                                         20
```